United States Patent
Cupps et al.

(12)

(10) Patent No.: US 6,391,878 B2
(45) Date of Patent: May 21, 2002

(54) GUANIDINYL HETEROCYCLE COMPOUNDS USEFUL AS ALPHA-2 ADRENOCEPTOR AGONISTS

(75) Inventors: Thomas Lee Cupps, Norwich, NY (US); Sophie Eva Bogdan, Maineville, OH (US); Raymond Todd Henry, Pleasant Plain, OH (US); Russell James Sheldon, Fairfield, OH (US); William Lee Seibel; Jeffrey Joseph Ares, both of Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/727,900

(22) Filed: Dec. 1, 2000

Related U.S. Application Data

(62) Division of application No. 09/308,788, filed on Aug. 9, 1999.
(60) Provisional application No. 60/032,023, filed on Nov. 25, 1996.

(51) Int. Cl.$^7$ .................. A61K 31/50; A61K 31/47; C07D 241/36; C07D 215/16
(52) U.S. Cl. .................. 514/249; 514/312; 514/313; 514/314; 544/353; 544/354; 544/355; 544/356; 546/156
(58) Field of Search .................. 546/156; 514/249, 514/312, 313, 314; 544/354, 355, 356, 353

(56) References Cited

U.S. PATENT DOCUMENTS

| | | | | |
|---|---|---|---|---|
| 3,890,319 A | | 6/1975 | Danielewicz et al. ........ 260/250 |
| 3,908,013 A | * | 9/1975 | Hughes | |
| 3,947,455 A | * | 3/1976 | Hughes | |
| 4,000,279 A | * | 12/1976 | Hughes | |
| 5,091,528 A | | 2/1992 | Gluckoswki ................. 544/105 |
| 5,541,210 A | | 7/1996 | Cupps et al. ................ 514/394 |
| 6,057,329 A | | 5/2000 | Davis et al. ................. 514/267 |

FOREIGN PATENT DOCUMENTS

| WO | WO 95/16449 | 6/1995 |
|---|---|---|
| WO | WO 98/23596 | 6/1998 |

OTHER PUBLICATIONS

CA 83:188388, hughes, 1975.*
CA 107:77202, Taylor, 1986.*
CA 125:264954, Acheampong, 1996.*
CA 123:217719, 1995.*
C.B. Chapleo, et al, "Heteroaromatic Analogues of the $\alpha_2$–Adrenoceptor Partial Agonist Clonidine", *J. Med. Chem.*, vol. 32, pp. 1627–1630, (1989).
Timmermans, P.B.M.W.M, et al, "12.1 $\alpha$–Adrenergic Receptors", *Neurotransmitter and Autocoid Receptors*, pp. 133–185.
Clare, K.A., et al., Effects of $\alpha_2$–Adrenoceptor Agonists and of Related Compounds on Aggregation of, and on Adenylate Cyclase Activity in, Human Platelets, *Br. J. Pharmac*, vol. 82, pp. 467–476, (1984).
Chapleo, C.B., "Effect of 1,4–Dioxanyl Substitution on the Adrenergic Activity of Some Standard $\alpha$–Adrenoreceptor Agents", *Eur. J. Med. Chem.*, vol. 24, pp. 619–622, (1989).
Van Meel, J.C.A., "Selectivity of Some Alpha Adrenoceptor Agonists for Peripheral Alpha–1 and Alpha–2 Adrenoceptors in the Normotensive Rat[1]", *The Journal of Pharmacology and Experimental Therapeutics*, vol. 219, No. 3, pp. 760–767, (1981).
Timmerman, P.B.M.W.M., et al., "Quantitative Relationships Between $\alpha$–Adrenergic Activity and Binding Affinity of $\alpha$–Adrenoceptor Agonists and Antagonists", *J. Med. Chem.*, vol. 27, pp. 495–503, (1984).
Megens, A.A.H.P., et al., "Further Validation of in vivo and in vitro Pharmacological Procedures for Assessing the $\alpha_2/\alpha_1$–selectivity of Test Compounds: (2) $\alpha$–adrenoceptor Agonists", *European Journal of Pharmacology*, vol. 129, pp. 57–64, (1986).
Timmermans, P.B.M.W.M., et al., "$\alpha$–Adrenoceptor Agonists and Antagonists", *Drugs of the Future*, vol. 9, No. 1, pp. 41–55, (1984).
Ruffolo, R.R., et al., "Pharmacological & Therapeutic Applications of Alpha–2 Adrenoceptor Subtypes", *Annual Review of Pharmacology & Toxicology*, vol. 32, pp. 243–279, (1993).
*Chemical Abstracts*, 102: 168273, 1984.
*Chemical Abstracts*, 132: 260666, Dykens, 2000.
*Chemical Abstracts*, 132:233047, Hasegawa, 2000.

* cited by examiner

*Primary Examiner*—D. Margaret Seaman
(74) *Attorney, Agent, or Firm*—David V. Upite; Mary Pat McMahon; Karen F. Clark

(57) ABSTRACT

This invention involves compounds having the following structure:

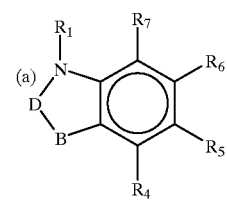

as described in the Claims; and enantiomers, optical isomers, stereoisomers, diastereomers, tautomers, addition salts, biohydrolyzable amides and esters thereof, as well as pharmaceutical compositions comprising such novel compounds. The invention also relates to the use of such compounds for preventing or treating disorders modulated by alpha-2 adrenoceptors.

40 Claims, No Drawings

GUANIDINYL HETEROCYCLE COMPOUNDS USEFUL AS ALPHA-2 ADRENOCEPTOR AGONISTS

CROSS REFERENCE

This application is a divisional of Ser. No. 09/308,788 filed Aug. 9, 1999, which claims priority under Title 35, United States Code 119(e) from Provisional Application Ser. No. 60/032,023, filed Nov. 25, 1996.

TECHNICAL FIELD

This invention relates to certain substituted guanidinyl heterocycle compounds. The compounds have been found to be alpha-2 adrenoceptor agonists and are useful for treatment of disorders modulated by alpha-2 adrenoceptors.

BACKGROUND OF THE INVENTION

Therapeutic indications of alpha-2 adrenoceptor agonists have been discussed in the literature: Ruffolo, R. R., A. J. Nichols, J. M. Stadel, & J. P. Hieble, "Pharmacologic and Therapeutic Applications of Alpha-2 Adrenoceptor Subtypes", *Annual Review of Pharmacology & Toxicology*, Vol. 32 (1993) pp. 243–279.

Information regarding alpha adrenergic receptors, agonists and antagonists, in general, and regarding compounds related in structure to those of this invention are disclosed in the following references: Timmermans, P. B. M. W. M., A. T. Chiu & M. J. M. C. Thoolen, "12.1 α-Adrenergic Receptors", *Comprehensive Medicinal Chemistry*, Vol. 3, Membranes & Receptors, P. G. Sammes & J. B. Taylor, eds., Pergamon Press (1990), pp. 133–185; Timmermans, P. B. M. W. M. & P. A. van Zwieten,"α-Adrenoceptor Agonists and Antagonists", *Drugs of the Future*, Vol. 9, No. 1, (January, 1984), pp. 41–55; Megens, A. A. H. P., J. E. Leysen, F. H. L. Awouters & C. J. E. Niemegeers, "Further Validation of in vivo and in vitro Pharmacological Procedures for Assessing the $\alpha_1$ and $\alpha_2$-Selectivity of Test Compounds: (2) α-Adrenoceptor Agonists", *European Journal of Pharmacology*, Vol.129 (1986), pp. 57–64; Timmermans, P. B. M. W. M., A. de Jonge, M. J. M. C. Thoolen, B. Wilffert, H. Batink & P. A. van Zwieten, "Quantitative Relationships between α-Adrenergic Activity and Binding Affinity of α-Adrenoceptor Agonists and Antagonists", *Journal of Medicinal Chemistry*, Vol. 27 (1984) pp. 495–503; van Meel, J. C. A., A. de Jonge, P. B. M. W. M. Timmermans & P. A. van Zwieten, "Selectivity of Some Alpha Adrenoceptor Agonists for Peripheral Alpha-1 and Alpha-2 Adrenoceptors in the Normotensive Rat", *The Journal of Pharmacology and Experimental Therapeutics*, Vol. 219, No. 3 (1981), pp. 760–767; Chapleo, C. B., J. C. Doxey, P. L. Myers, M. Myers, C. F. C. Smith & M. R. Stillings, "Effect of 1,4-Dioxanyl Substitution on the Adrenergic Activity of Some Standard α-Adrenoreceptor Agents", *European Journal of Medicinal Chemistry*, Vol. 24 (1989), pp. 619–622; Chapleo, C. B., R. C. M. Butler, D. C. England, P. L. Myers, A. G. Roach, C. F. C. Smith, M. R. Stillings & I. F. Tulloch, "Heteroaromatic Analogues of the $\alpha_2$-Adrenoreceptor Partial Agonist Clonidine", *Journal of Medicinal Chemistry*, Vol. 32 (1989), pp. 1627–1630; Clare, K. A., M. C. Scrutton & N. T. Thompson, "Effects of $\alpha_2$-Adrenoceptor Agonists and of Related Compounds on Aggregation of, and on Adenylate Cyclase Activity in, Human Platelets", *British Journal of Pharmacology*, Vol. 82 (1984), pp. 467–476; U.S. Pat. No. 3,890,319 issued to Danielewicz, Snarey & Thomas on Jun. 17, 1975; and U.S. Pat. No. 5,091,528 issued to Gluchowski on Feb. 25, 1992. However, many compounds related in structure to those of this invention do not provide the activity and specificity desirable when treating disorders modulated by alpha-2 adrenoceptors.

For example, many compounds found to be effective nasal decongestants are frequently found to have undesirable side effects, such as causing hypertension and insomnia at systemically effective doses. There is a need for new drugs which provide relief from nasal congestion without causing these undesirable side effects.

OBJECTS OF THE INVENTION

It is an object of the invention to provide compounds and compositions useful in treating disorders modulated by alpha-2 adrenoceptors.

It is an object of this invention to provide novel compounds having substantial activity in preventing or treating nasal congestion, otitis media, and sinusitis, without undesired side effects.

It is also an object of this invention to provide novel compounds for treating cough, chronic obstructive pulmonary disease (COPD) and/or asthma.

It is also an object of this invention to provide novel compounds for treating diseases and disorders associated with sympathetic nervous system activity, including benign prostatic hypertrophy, cardiovascular disorders comprising myocardial ischemia, cardiac reperfusion injury, angina, cardiac arrhythmia, heart failure and hypertension.

It is also an object of this invention to provide novel compounds for treating ocular disorders, such as ocular hypertension, glaucoma, hyperemia, conjunctivitis and uveitis.

It is also an object of this invention to provide novel compounds for treating gastrointestinal disorders, such as diarrhea, irritable bowel syndrome, hyperchlorhydria (hyperacidity) and peptic ulcer (ulcer).

It is also an object of this invention to provide novel compounds for treating migraine.

It is also an object of this invention to provide novel compounds for treating pain, substance abuse and/or withdrawal.

It is a still further object of this invention to provide such compounds which have good activity from peroral, parenteral, intranasal and/or topical dosing.

SUMMARY OF THE INVENTION

This invention relates to compounds having the following structure:

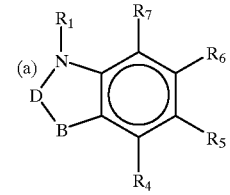

a) $R_1$ is hydrogen; or alkyl or nil; where $R_1$ is nil, bond (a) is a double bond;

b) D is $CR_2$ and $R_2$ is selected from hydrogen; unsubstituted $C_1$–$C_3$ alkanyl; amino, hydroxy, mercapto; $C_1$–$C_3$ alkylthio or alkoxy; $C_1$–$C_3$ alkylamino or $C_1$–$C_3$ dialkylamino and halo; or when B is $CR_3$; D may be N;

c) B is $NR_9$, $CR_3$=$CR_8$, $CR_3$=N, $CR_3$, S, O, SO or $SO_2$; wherein Rg is selected from hydrogen; unsubstituted $C_1$–$C_3$ alkanyl, alkenyl or alkynyl; cycloalkanyl, cycloalkenyl; and wherein $R_3$ and $R_8$ are each independently selected from hydrogen; unsubstituted $C_1$-$C_3$ alkanyl, alkenyl or alkynyl; cycloalkanyl, cycloalkenyl; unsubstituted $C_1$-$C_3$ alkylthio or alkoxy; hydroxy; thio; nitro; cyano; amino; $C_1$-$C_3$ alkylamino or $C_1$-$C_3$ dialkylamino and halo;

d $R_4$, $R_5$ and $R_6$ are each independently selected from hydrogen; unsubstituted $C_1$-$C_3$ alkanyl, alkenyl or alkynyl; cycloalkanyl, cycloalkenyl; unsubstituted $C_1$-$C_3$ alkylthio or alkoxy; hydroxy; thio; nitro; cyano; amino; $C_1$-$C_3$ alkylamino or $C_1$-$C_3$ dialkylamino; halo; and NH—C(=NR$_{10}$)NHR$_{11}$ (guanidinyl); wherein $R_{10}$ and $R_{11}$ are independently selected from hydrogen; methyl; and ethyl; and wherein one and only one of $R_4$, $R_5$ and $R_6$ is guanidinyl;

e) $R_7$ is selected from hydrogen; unsubstituted $C_1$-$C_3$ alkanyl, alkenyl or alkynyl; cycloalkanyl, cycloalkenyl; unsubstituted $C_1$-$C_3$ alkylthio or alkoxy; hydroxy; thio; nitro; cyano; amino; $C_1$-$C_3$ alkylamino or $C_1$-$C_3$ dialkylamino and halo;

and enantiomers, optical isomers, stereoisomers, diastereomers, tautomers, addition salts, biohydrolyzable amides and esters, and pharmaceutical compositions containing such novel compounds, and the use of such compounds for preventing or treating disorders modulated by alpha-2 adrenoceptors.

DETAILED DESCRIPTION OF THE INVENTION

As used herein, "alkanyl" means a saturated hydrocarbon substituent, straight or branched chain, unsubstituted or substituted.

As used herein, "alkenyl" means a hydrocarbon substituent with one double bond, straight or branched chain, unsubstituted or substituted.

As used herein, "alkylthio" means a substituent having the structure Q—S—, where Q is alkanyl or alkenyl.

As used herein, "alkoxy" means a substituent having the structure Q—O—, where Q is alkanyl or alkenyl.

As used herein, "alkylamino" means a substituent having the structure Q—NH—, where Q is alkanyl or alkenyl.

As used herein, "dialkylamino" means a substituent having the structure $Q_1$—N($Q_2$)—, where each Q is independently alkanyl or alkenyl.

"Guanidinyl" is defined as a radical of structure;

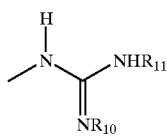

For purposes of exemplifying this radical, wherever it appears in a chart, it is shown as "GNDNL" for brevity.

"Halo", "halogen", or "halide" is a chloro, bromo, fluoro or iodo.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, incorporated by reference herein. Preferred cationic salts include the alkali metal salts (such as sodium and potassium), alkaline earth metal salts (such as magnesium and calcium) and organic salts. Preferred anionic salts include halides, sulfonates, carboxylates, phosphates, and the like. Clearly contemplated in such salts are addition salts that may provide an optical center, where once there was none. For example, a chiral tartrate salt may be prepared from the compounds of the invention, and this definition includes such chiral salts.

The compounds of the invention are sufficiently basic to form acid-addition salts. The compounds are useful both in the free base form and the form of acid-addition salts, and both forms are within the purview of the invention. The acid-addition salts are in some cases a more convenient form for use. In practice, the use of the salt form inherently amounts to the use of the base form of the active. Acids used to prepare acid-addition salts include preferably those which produce, when combined with the free base, medicinally acceptable salts. These salts have anions that are relatively innocuous to the animal organism, such as a mammal, in medicinal doses of the salts so that the beneficial property inherent in the free base are not vitiated by any side effects ascribable to the acid's anions.

Examples of appropriate acid-addition salts include, but at not limited to hydrochloride, hydrobromide, hydroiodiode, sulfate, hydrogensulfate, acetate, trifluoroacetate, nitrate, maleate, citrate, fumarate, formate, stearate, succinate, mallate, malonate, adipate, glutarate, lactate, propionate, butyrate, tartrate, methanesulfonate, trifluoromethanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds are prepared by several methods. For example the free base can be dissolved in an aqueous alcohol solution containing the appropriate acid and the salt is isolated by evaporation of the solution. Alternatively, they may be prepared by reacting the free base with an acid in an organic solvent so that the salt separates directly. Where separation of the salt is difficult, it can be precipitated with a second organic solvent, or can be obtained by concentration of the solution.

Although medicinally acceptable salts of the basic compounds are preferred, all acid-addition salts are within the scope of the present invention. All acid-addition salts are useful as sources of the free base form, even if the particular salt per se is desired only as an intermediate product. For example, when the salt is formed only for purposes of purification or identification, or when it is used as an intermediate in preparing a medicinally acceptable salt by ion exchange procedures, these salts are clearly contemplated to be a part of this invention.

"Biohydrolyzable amide" refers to an amide of the compound of the invention that is readily converted in vivo by a mammal subject to yield an active compound of the invention.

A "biohydrolyzable ester" refers to an ester of the compound of the invention that is readily converted by a mammal subject to yield an active compound of the invention.

"Optical isomer", "stereoisomer", "enantiomer," "diastereomer," as referred to herein have the standard art recognized meanings (Cf., *Hawleys Condensed Chemical Dictionary*, 11th Ed.). Of course, an addition salt may provide an optical center, where once there was none. For example, a chiral tartrate salt may be prepared from the compounds of the invention, and this definition includes such chiral salts. It will be apparent to the skilled artisan that disclosure of the racemic mixture alone discloses any enantiomers therein. Thus by one disclosure, more than one compound is taught.

As used herein "animal" includes "mammals" which includes "humans".

The skilled artisan will appreciate that tautomeric forms will exist in certain compounds of the invention. For example, when $R_2$ is hydroxy and bond (a) is a double bond, it is understood to include the keto form of that molecule, where $R_2$ is oxo, and bond (a) is a single bond, though not specifically described. Thus, in this description the disclosure of one tautomeric form discloses each and all of the tautomers. Similarly, when tautomer A of the molecule is shown, it is understood to include tautomers B and C of that molecule although not specifically depicted.

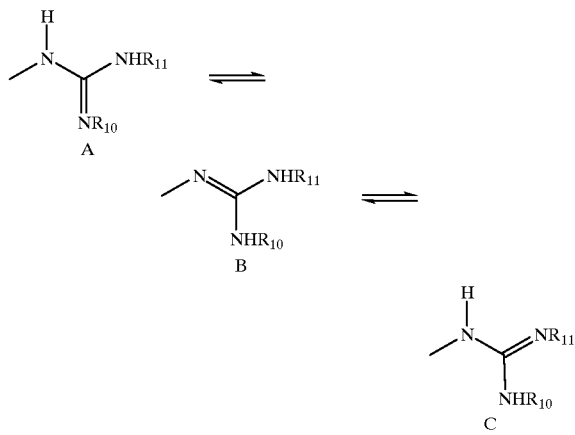

The illustration of specific protected forms and other derivatives of the Formula (I) compounds is not intended to be limiting. The application of other useful protecting groups, salt forms, etc. is within the ability of the skilled artisan.

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyacetyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

For the purposes of nomenclature, as shown in the following example, the location of the guanidinyl radical is:

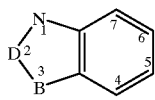

It is recognized that where B is $CR_3=CR_8$ and the like, this numbering is not in strict compliance with IUPAC nomenclature. It is used for illustration of synthetic methods only; examples of compounds have names which more closely resemble IUPAC nomenclature.

Compounds

This invention includes compounds having the following structure:

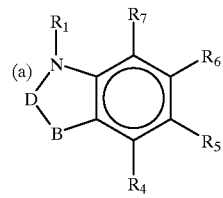

as described in the Summary of the Invention.

In the above structure, when the guanidinyl is at the 6-position, preferably $R_7$ is selected from hydrogen; unsubstituted alkanyl or alkenyl having from 1 to about 3 carbon atoms; unsubstituted alkylthio or alkoxy having from 1 to about 3 carbon atoms; hydroxy; thiol; cyano; and halo. $R_4$ is preferably hydrogen, cyano, halo or methyl. $R_7$ is also preferably alkanyl, more preferably methyl or ethyl, most preferably methyl. $R_7$ which is alkylthio or alkoxy is preferably saturated, also preferably $C_1$ or $C_2$, most preferably methylthio or methoxy. $R_7$ which is halo is preferably chloro or bromo.

In the above structure, when the guanidinyl is at the 5-position, preferably $R_4$ is selected from hydrogen; unsubstituted alkanyl or alkenyl having 1 to about 3 carbon atoms; unsubstituted alkylthio or alkoxy having from 1 to about 3 carbon atoms; hydroxy; thiol; cyano; and halo. $R_7$ is preferably alkanyl or halo. $R_4$ and $R_7$ are most preferably methyl.

In the above structure, when the guanidinyl is at the 4-position, preferably $R_7$ is selected from hydrogen; unsubstituted alkanyl or alkenyl having from 1 to about 3 carbon atoms; hydroxy; thiol; cyano; and halo. $R_7$ which is alkanyl, is preferably methyl or ethyl, more preferably methyl. $R_7$ which is halo is preferably chloro or bromo. $R_6$ is preferably hydrogen; alkanyl; cyano; and halo. $R_6$ which is alkanyl is preferably methyl or ethyl, most preferably methyl. $R_5$ is preferably hydrogen; alkanyl; and halo. $R_5$ which is alkanyl is preferably methyl or ethyl, most preferably methyl.

Preferred compounds of this invention have the following structure:

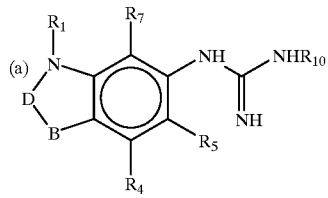

where $R_1$ is nil, (a) is a double bond and D, B, $R_4$, $R_5$, $R_7$ and $R_{10}$ are as indicated in the following table:

| Compound No | D | B | $R_4$ | $R_5$ | $R_7$ | $R_{10}$ |
|---|---|---|---|---|---|---|
| 1 | CH | NH | H | H | Me | H |
| 2 | CH | NH | Me | H | Me | H |
| 3 | CH—Me | NH | H | H | Me | H |
| 4 | CH | N—Me | H | H | Me | H |
| 5 | CH | NH | H | H | Br | H |
| 6 | CH | NH | H | H | Me | Me |
| 7 | CH | CH=CH | H | H | Me | H |
| 8 | CH | CH=CH | H | H | Br | H |

-continued

| Compound No | D | B | $R_4$ | $R_5$ | $R_7$ | $R_{10}$ |
|---|---|---|---|---|---|---|
| 9 | CH | S | H | Me | H | H |
| 10 | CH | S | H | H | Br | H |

Methods of making the compounds of the invention

The compounds of this invention are synthesized using the following procedures. For purposes of this description, 6-guanidinyl compounds are shown, but the skilled artisan will appreciate that the 4- and 5-guanidinyl compounds are prepared similarly. The $R_1$–$R_7$ radicals are omitted for clarity, unless they are prepared in that specific scheme. The skilled artisan will appreciate that the radicals omitted are added using techniques known in the art. The skilled artisan will also appreciate that the methods described may be used with blocking groups and the like, as appropriate.

Guanidinyl groups are conveniently prepared from nitro and amino compounds via the following example synthetic sequences:

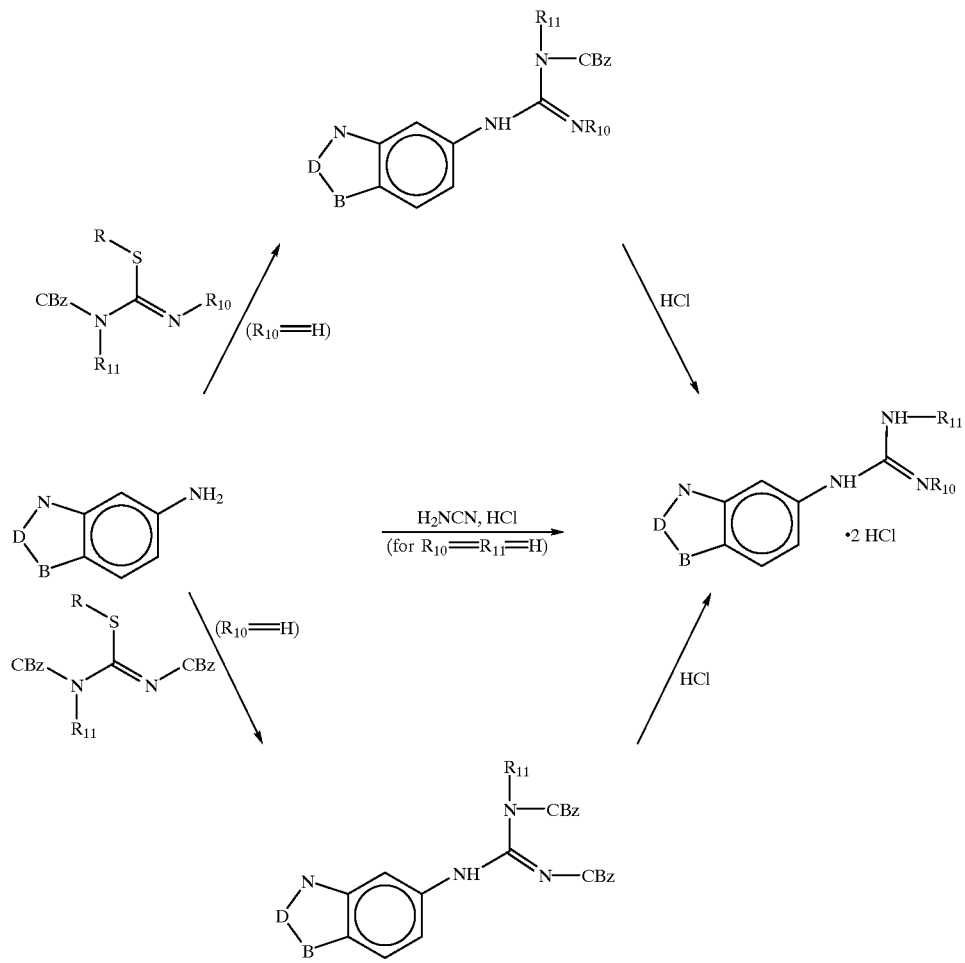

Preferably these compounds are made from nitro or amino compounds. (Nitro and amino compounds are made by known processes.) The compounds may be manipulated to result in the suitably substituted aminoheterocycle. This aminoheterocycle is then subjected to known methods to produce the guanidinyl derivative. For example, the amino compound may be reacted with cyanamide ($H_2NCN$) in acid to provide the guanidinyl compound. Alternatively, the amino compound may be reacted with a guanidine precursor, such as an alkyl pseudothiourea or protected alkyl pseudothiourea in the presence of a mercuric salt or the like.

The above starting nitro and amino compounds are obtained via one or more synthetic steps comprising alkylations, halogenations (usually brominations), and halogen displacement reactions. These reaction types are summarized below;

ALKYLATION REACTION
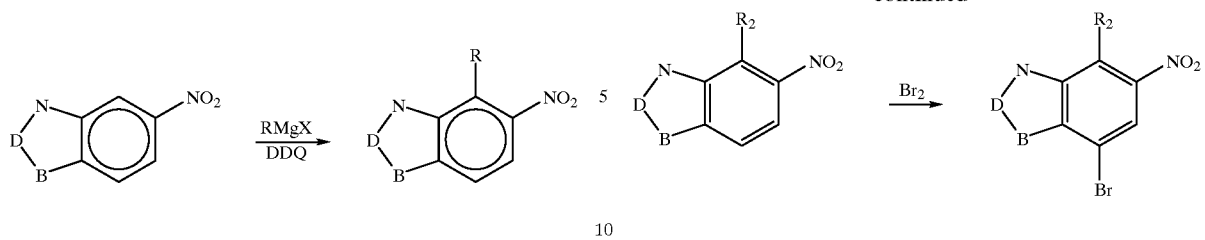
FLUORINATION
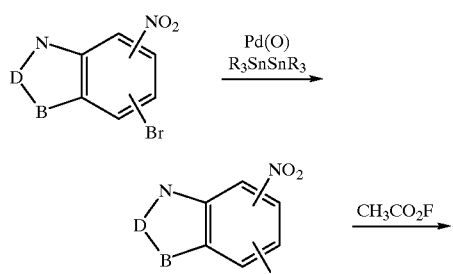
HALOGENATION, PREFERABLY BROMINATION
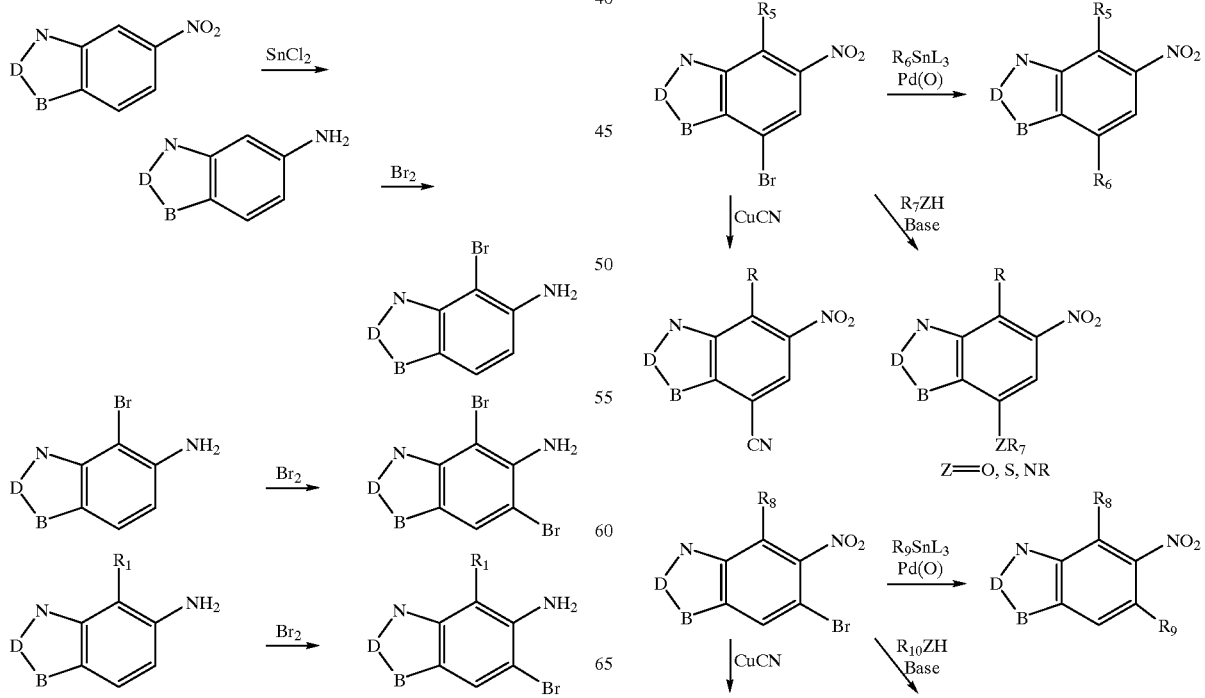
Preferably, chlorination is accomplished using $Cl_2$, and iodination, by ICl using the same reactions.
HALOGEN DISPLACEMENT REACTIONS
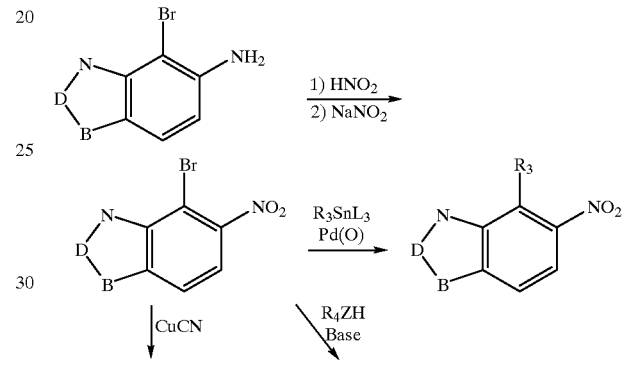

-continued

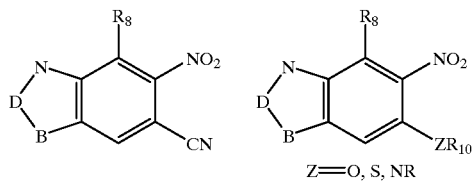

Z=O, S, NR

It will be apparent to the skilled artisan that the reactions illustrated above are known reactions. Furthermore, it is within the purview of the skilled artisan to vary these reactions to prepare compounds within the scope of the claims.

In the above schemes, where an R is alkoxy or alkylthio, the corresponding hydroxy or thiol compounds are derived from the final compounds by using a standard dealkylating procedure (Bhatt, et al., "Cleavage of Ethers", *Synthesis*, 1983, pp. 249–281).

The starting materials used in preparing the compounds of the invention are known, made by known methods, or are commercially available as a starting material.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterifications and saponifications and the like. These manipulations are discussed in standard texts such as March, *Advanced Organic Chemistry* (Wiley), Carey and Sundberg, *Advanced Organic Chemistry* (2 vol.) and Trost and Fleming *Comprehensive Organic Synthesis* (6 vol.). The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations are found, for example, in T. Greene, *Protecting Groups in Organic Synthesis*.

COMPOUND EXAMPLES

The following non-limiting examples provide details for the synthesis of guanidinyl heterocycles:

Example 1

(4-Methylbenzimidazol-5-yl)guanidine

A. 2,3-Diamino-6-nitrotoluene.

To a solution of 30 g of 3-methyl-2,4-dinitroaniline in 750 mL of boiling ethanol is added dropwise over 90 minutes a solution of 109.6 g of sodium sulfide nonahydrate in 750 mL of water. At the end of the addition, the mixture is heated to reflux for 30 minutes then poured into ice (2000 g) and allowed to stand until all the ice has melted. The mixture is then extracted with methylene chloride and the organic layer is dried over magnesium sulfate and rotary evaporated. The residue is purified by flash column chromatography on silica gel, eluting with methylene chloride to afford 2,3-diamino-6-nitrotoluene as an orange solid.

B. 4-Methyl-5-nitrobenzimidazole.

A mixture of 11.8 g of 2,3-diamino-6-nitrotoluene, 390 mL of 88% formic acid and 38 mL of 12N hydrochloric acid is heated to reflux for 1 hour. The resulting mixture is cooled to room temperature and rotary evaporated. The residue is diluted with 200 mL of water, then basified with ammonium hydroxide (28–30%). The suspension is extracted with ethyl acetate (3×200 mL). The combined extracts are dried over magnesium sulfate and rotary evaporated to provide 4-methyl-5-nitrobenzimidazole as an orange solid.

C. 1-tert-Butoxycarbonyl-4-methyl-5-nitrobenzimidazole.

A suspension of 11.2 g of 4-methyl-5-nitrobenzimidazole, 21.58 g of di-tert-butyl-dicarbonate, 11.7 mL of triethylamine and 100 mg of 4-dimethylamino-pyridine in methanol (800 mL) and ethyl acetate (400 mL) is stirred at room temperature overnight. The mixture is rotary evaporated and the residue purified by flash column chromatography on silica gel, eluting with 10% ethyl acetate in hexanes. The product-containing fractions are combined and rotary evaporated to afford a white solid contaminated with a yellow oil. The solid is dissolved in methylene chloride and enough hexane is added to cause precipitation. The solid is filtered and washed with 50% methylene chloride/hexane. The filtrate is rotary evaporated and the process repeated until no more clean white solid is obtained by precipitation. The combined solid fractions are dried in vacuo to afford 1-tert-butoxycarbonyl-4-methyl-5-nitrobenzimidazole as a white solid.

D. 5-Amino-1-tert-butoxycarbonyl-4-methylbenzimidazole.

To a solution of 8 g of 1-tert-butoxycarbonyl-4-methyl-5-nitrobenzimidazole in 40 mL of methanol and 400 mL of ethyl acetate are added 500 mg of palladium-on-carbon (10%) and 7.27 g of ammonium formate. The mixture is stirred at 50° C. for 2 hours, then filtered on Celite, with a methanol wash of the solids. The filtrate is rotary evaporated and the residue partitioned between water and ethyl acetate. The organic layer is washed with saturated ammonium chloride, dried over magnesium sulfate, filtered and rotary evaporated to afford pure 5-amino-1-tert-butoxycarbonyl-4-methylbenzimidazole as an off-white solid.

E. 1-(tert-Butyloxycarbonyl)-5-[$N^2$,$N^3$-bis(benzyloxycarbonyl)guanidino]-4-methylbenzimidazole.

To a solution of 500 mg of 5-amino-1-(tert-butoxycarbonyl)-4-methyl-benzimidazole in 20 mL of tetrahydrofuran are added 753 mg of ethyl N,N-bis(benzyloxycarbonyl)pseudothiourea and 645 mg of mercuric acetate and the mixture is stirred at room temperature for 1 hour. The resulting suspension is diluted with ethyl acetate and washed with water followed by brine. The aqueous layers are extracted with ethyl acetate; the combined organic layers are dried over magnesium sulfate, filtered and rotary evaporated. The residue is purified by flash column chromatography on silica gel, eluting with 50% ethyl acetate/hexanes followed by recrystallization from hexanes/methylene chloride to provide 927 mg of 1-(tert-butyloxycarbonyl)-5-[$N^2$, $N^3$-bis(benzyloxycarbonyl)-guanidino]-4-methylbenzimidazole as a white solid.

F. 5-[$N^2$,$N^3$-Bis(benzyloxycarbonyl)quanidino]-4-methylbenzimidazole.

To a cold (0° C.) solution of 874 mg of 1-(tert-butoxycarbonyl)-5-[$N^2$, $N^3$-bis(benzyloxycarbonyl)guanidino]-4-methylbenzimidazole in 2 mL of methylene chloride is added 2 mL of trifluoroacetic acid. The resulting solution is stirred at room temperature for 30 minutes, then rotary evaporated. The residue is purified by flash column chromatography on silica gel, eluting with 20% methanol/ chloroform followed by recrystallization from hexanes/methylene chloride to provide 573 mg of 5-[$N^2,N^3$-bis(benzyloxycarbonyl)guanidino]-4-methylbenzimidazole as a white solid.

G. (4-Methylbenzimidazol-5-yl)guanidine, dihydrochloric acid salt.

To a solution of 740 mg of 5-[$N^2,N^3$-bis(benzyloxycarbonyl)guanidino]-4-methyl-benzimidazole in 20 mL of ethanol are added 240 mg of ammonium formate and a catalytic amount of palladium-on-carbon. The resulting suspension is stirred at room temperature for 10 hours. The reaction mixture is filtered and the filtrate is rotary evaporated. The residue is dissolved in 25 mL of methanol and treated with a slow stream of hydrogen chloride gas for about 5 minutes. The resulting solution is stirred at room temperature for 2 hours and rotary evaporated to give a pale yellow solid. The solid is purified by recrystallization from methanol/ethyl acetate to provide 361 mg of (4-methylbenzimidazol-5-yl)guanidine, dihydrochloric acid salt as a yellow solid.

Example 2

(4,7-Dimethylbenzimidazol-5-yl)guanidine

A. 4,7-Dimethylbenzimidazole.

A mixture of 5.1 g of 2,3-diamino-p-xylene, 200 mL of 88% formic acid and 20 mL of 12N hydrochloric acid is heated to reflux for 3 hours. The resulting mixture is cooled to room temperature and rotary evaporated. The residue is diluted with 100 mL of water, then basified with ammonium hydroxide (28–30%). The suspension is extracted with ethyl acetate (3×100 mL). The combined extracts are dried over magnesium sulfate and rotary evaporated to afford 4,7-dimethylbenzimidazole as a yellow solid.

B. 4,7-Dimethyl-5-nitrobenzimidazole.

To a cold (ice bath) solution of 1 g of 4,7-dimethylbenzimidazole in 8 mL of concentrated sulfuric acid is added dropwise concentrated nitric acid (0.37 mL), over 50 minutes. The mixture is stirred an additional 30 minutes in the ice bath, then poured into a mixture of crushed ice (30 mL) and ammonium hydroxide (30 mL). The resulting mixture is extracted with ethyl acetate. The extract is dried over magnesium sulfate and rotary evaporated to afford 4,7-dimethyl-5-nitrobenzimidazole as a dark tan solid.

C. 5-Amino-4,7-dimethylbenzimidazole.

To a solution of 1.17 g of 4,7-dimethyl-5-nitrobenzimidazole in 150 mL of methanol are added 160 mg of palladium-on-carbon (10%) and 1.31 g of ammonium formate. The mixture is stirred at room temperature overnight, then filtered on Celite, with a methanol wash of the solids. The filtrate is rotary evaporated and the residue partitioned between water and ethyl acetate. The organic layer is washed with saturated ammonium chloride, dried over magnesium sulfate, filtered and rotary evaporated to afford 5-amino-4,7-dimethylbenzimidazole as a foamy reddish solid.

D. 5-[$N^2$,N3-bis(benzyloxycarbonyl)guanidino]-4,7-dimethybenzimidazole.

To a solution of 430 mg of 5-amino-4,7-dimethylbenzimidazole in 100 mL of ethyl acetate and 10 mL of methanol are added 19 g of ethyl N,N-bis(benzyloxycarbonyl)pseudothiourea and 855 mg of mercuric acetate and the mixture is stirred at room temperature for 15 hours. The mixture is rotary evaporated and the residue is purified by flash column chromatography on silica gel, eluting with 5% methanol/ethyl acetate to provide 1.01 g of 5-[$N^2,N^3$-bis(benzyloxycarbonyl)guanidino]-4,7-dimethybenzimidazole as a glassy solid.

E. (4,7-Dimethylbenzimidazol-5-yl)guanidine, dihydrobromic acid salt.

To a solution of 1 g of 5-[$N^2,N^3$-bis(benzyloxycarbonyl)guanidino]-4,7-dimethyl-benzimidazole in 100 mL of 1/1 ethyl acetate/methanol is added a catalytic amount of palladium-on-carbon. The resulting suspension is stirred at room temperature under hydrogen at atmospheric pressure for 15 hours. The reaction mixture is filtered on Celite with a methanol wash of the solids and the filtrate is rotary evaporated. The residue is dissolved in 50 mL of methanol and treated with 0.85 mL of 30% hydrobromic acid/acetic acid for about 5 minutes. The resulting solution is rotary evaporated and the residue is purified by recrystallization from ethanol/ether to provide 490 mg of (4,7-dimethylbenzimidazol-5-yl)guanidine dihydrobromic acid salt as a white solid.

Example 3

(2,4-Dimethylbenzimidazol-5-yl)quanidine

A. 2,4-Dimethyl-5-nitrobenzimidazole.

A mixture of 668 mg of 2,3-diamino-6-nitrotoluene, 20 mL of glacial acetic acid and 2 mL of 12N hydrochloric acid is heated to reflux for 3 hours. The resulting mixture is cooled to room temperature and rotary evaporated. The residue is diluted with 20 mL of water, and basified with ammonium hydroxide (28–30%). The resulting suspension is extracted with ethyl acetate and the extracts are dried over magnesium sulfate, filtered and rotary evaporated to provide 720 mg of 2,4-dimethyl-5-nitrobenzimidazole as a tan solid.

B. 5-Amino-2,4-dimethylbenzimidazole.

To a solution of 700 mg of 2,4-dimethyl-5-nitrobenzimidazole in 50 mL of methanol is added a catalytic amount of palladium-on-carbon. The resulting suspension is stirred at room temperature under hydrogen at atmospheric pressure for 15 hours. The reaction mixture is filtered on Celite with a methanol wash of the solids and the filtrate is concentrated. The residue is purified by flash column chromatography on silica gel, eluting with 5% methanol/ethyl acetate to provide 565 mg of 5-amino-2,4-dimethybenzimidazole as a tan solid.

C. (2,4-Dimethylbenzimidazol-5-yl)guanidine, dihydrochloric acid salt.

To 565 mg of 5-amino-2,4-dimethylbenzimidazole is added 0.75 mL of concentrated hydrochloric acid and 0.38 mL of water. The resulting mixture is stirred at room temperature for 5 minutes to give a homogeneous paste. To this mixture are added 589 mg of cyanamide and the mixture is stirred at 70° C. for 3 hours. The reaction mixture is cooled to 0° C. and 1 mL of water and 0.5 mL of concentrated hydrochloric acid are added. The mixture is stirred at 0° C. for 30 minutes and rotary evaporated. The residue is dissolved in 10 mL of methanol and precipitated with ether to provide 594 mg of (2,4-dimethylbenzimidazol-5-yl)guanidine, dihydrochloric acid salt as a white solid.

Example 4

(1,4-Dimethylbenzimidazol-5-yl)quanidine

A. 2,4-Dinitro-3-methyl-formanilide.

To a solution of 2 g of 2,4-dinitro-3-methylaniline in 10 mL of 99% formic acid heated at 55° C., are added dropwise 2.5 mL of acetic anhydride, over 15 minutes. The mixture is stirred for 1 hour at 55° C. then cooled to room temperature and rotary evaporated. The residue is diluted with 100 mL of ethyl acetate, washed with saturated aqueous sodium bicarbonate, dried over magnesium sulfate and rotary evaporated. The residue is purified by flash column chromatography on silica gel, eluting with chloroform, to afford 2,4-dinitro-3-methyl-formanilide as a white solid.

C. N,3-Dimethyl-2,4-dinitroaniline.

To a solution of 1.15 g of 2,4-dinitro-3-methyl-formanilide in 40 mL of dry tetrahydrofuran are added 1.21 mL of borane-dimethyl sulfide complex. The mixture is heated to reflux for 2 hours, then cooled in an ice bath; 30 mL of methanol are added and the stirring is maintained for 1 hour at 0° C. The mixture is acidified to pH=2 with concentrated hydrochloric acid and heated to reflux for 1 hour, diluted with 70 mL of methanol and rotary evaporated. The solid residue is suspended in 150 mL of water and basified to pH=12 with concentrated sodium hydroxide. The mixture is extracted with chloroform, and the organic layer is dried over potassium carbonate and rotary evaporated. The residue is purified by flash column chromatography on silica gel, eluting with 25% ethyl acetate/hexane to afford N,3-dimethyl-2,4-dinitroaniline as an orange solid.

D. N,3-Dimethyl-2,4-dinitroformanilide.

To a solution of 450 mg of N,3-dimethyl-2,4-dinitroaniline in 10 mL of 99% formic acid and 4 mL of chloroform heated to 55° C., is added dropwise 1 mL of acetic anhydride in two portions at 1 hour intervals. The mixture is stirred for 5 hours at 55° C., then cooled to room temperature, poured into 50 mL of 1N sodium hydroxide and basified to pH=12 with concentrated sodium hydroxide. The mixture is extracted with methylene chloride, and the organic layer is dried over magnesium sulfate and rotary evaporated. The residue is purified by flash column chromatography on silica gel, eluting with chloroform, to afford N,3-dimethyl-2,4-dinitroformanilide as a white solid.

E. 2,4-Diamino-N,3-dimethylformanilide.

To a solution of 440 mg of N,3-dimethyl-2,4-dinitroformanilide in 40 mL of 3/1 methanol/ethyl acetate are added 95 mg of palladium-on-carbon (10%) and 930 mg of ammonium formate, and the mixture is stirred for 2 hours at room temperature. The mixture is filtered on Celite, with a methanol wash of the solids, and the filtrate is rotary evaporated. The residue is partitioned between methylene chloride and water. The aqueous layer is extracted 4 times with methylene chloride. The combined organic layers are dried over magnesium sulfate and rotary evaporated to afford 2,4-diamino-N,3-dimethylformanilide as a brown solid.

F. 5-Amino-1,4-dimethylbenzimidazole.

A suspension of 240 mg of 2,4-diamino-N,3-dimethylformanilide in 10 mL of 2N hydrochloric acid is heated to reflux for 90 minutes. The mixture is diluted with water (50 mL), basified with 1 N sodium hydroxide and extracted with ethyl acetate. The organic layer is dried over magnesium sulfate and rotary evaporated to afford 5-amino-1,4-dimethylbenzimidazole.

G. 5-[$N^2,N^3$-bis(benzyloxycarbonyl)guanidino]-1,4-dimethybenzimidazole.

To a solution of 250 mg of 5-amino-1,4-dimethylbenzimidazole in 75 mL of ethyl acetate and 10 mL of methanol are added 789 mg of ethyl N,N-bis (benzyloxycarbonyl)pseudothiourea and 665 mg of mercuric acetate and the mixture is stirred at room temperature for 15 hours. The mixture is filtered on Celite and rotary evaporated. The residue is purified by flash column chromatography on silica gel, eluting with 5% methanol/ethyl acetate to provide 590 mg of 5-[$N^2,N^3$-bis (benzyloxycarbonyl)guanidino]-1,4-dimethybenzimidazole as a white solid.

H. (1,4-Dimethylbenzimidazol-5-yl)guanidine, dihydrobromic acid salt.

To a solution of 530 mg of 5-[$N^2,N^3$-bis (benzyloxycarbonyl)guanidino]-1,4-dimethylbenzimidazole in 60 mL of 1/1 ethyl acetate/methanol is added a catalytic amount of palladium-on-carbon. The resulting suspension is stirred at room temperature under hydrogen at atmospheric pressure for 15 hours. The reaction mixture is filtered on Celite with a methanol wash of the solids and the filtrate is rotary evaporated. The residue is dissolved in 10 mL of methanol and treated with 0.2 mL of 30% hydrobromic acid/acetic acid for about 5 minutes. The resulting solution is rotary evaporated and the residue is purified by recrystallization using ethanol/ether to provide 30 mg of (1,4-dimethylbenzimidazol-5-yl)guanidine, dihydrobromic acid salt as a white solid.

Example 5

(4-Bromobenzimidazol-5-yl)guanidine

A. 5-Amino-4-bromobenzimidazole.

To a solution of 1.08 g of 5-aminobenzimidazole in 20 mL of glacial acetic acid are added 2.68 g of sodium acetate. To this solution is added dropwise 0.4 mL of bromine. The resulting brown precipitate is stirred at room temperature for 2 hours. The reaction mixture is rotary evaporated and the residue is diluted with water and ethyl acetate. The mixture is basified with 1 N sodium hydroxide and decanted. The organic layer is washed with water followed by brine. The aqueous layers are extracted with ethyl acetate; the combined organic layers are dried over magnesium sulfate, filtered and rotary evaporated. The residue is purified by flash column chromatography on silica gel, eluting with 12.5 to 16.5% methanol/methylene chloride followed by recrystallization from hexanes/ethyl acetate to provide 887 mg of 5-amino-4-bromobenzimidazole as a pale brown solid.

B. (4-Bromobenzimidazol-5-yl)guanidine, dihydrochloric acid salt.

To 637 mg of 5-amino-4-bromobenzimidazole are added 0.5 mL of concentrated hydrochloric and 0.25 mL of water. The resulting mixture is stirred at room temperature for 5 minutes to give a homogeneous paste. To this mixture are added 531 mg of cyanamide and the mixture is stirred at 80° C. for 1 hour. The reaction mixture is cooled to 0°C. and 0.5 mL of water and 1 mL of concentrated hydrochloric acid are added. The mixture is stirred at 0° C. for 30 minutes and rotary evaporated. The residue is dissolved in hot methanol and precipitated using hot ethyl acetate to provide 766 mg of (4-bromobenzimidazol-5-yl)guanidine, dihydrochloric acid salt as an off-white solid.

Example 6

$N^1$-Methyl-$N^2$-(4-methylbenzimidazol-5-yl) quanidine

A. 1-(tert-Butyloxycarbonyl)-5-[$N^2,N^3$-bis (benzyloxycarbonyl)-$N^2$-methylguanidino]-4-methylbenzimidazole.

To a solution of 600 mg of 5-amino-1-(tert-butoxycarbonyl)-4-methylbenzoimidazole in 20 mL of tetrahydrofuran are added 938 mg of ethyl N,N-bis (benzyloxycarbonyl)-N-methylpseudothiourea and 773 mg of mercuric acetate and the mixture is stirred at room temperature for 1 hour. The suspension is diluted with ethyl acetate and washed with water followed by brine. The aqueous layers are extracted with ethyl acetate; the combined organic layers are dried over magnesium sulfate, filtered and rotary evaporated. The residue is purified by flash column chromatography on silica gel, eluting with 50% ethyl acetate/hexanes followed by recrystallization from hexanes/methylene chloride to provide 927 mg of 1-(tert-butyloxycarbonyl)-5-[$N^2$, $N^3$-bis (benzyloxycarbonyl)-$N^2$-methylguanidino]-4-methylbenzimidazole as a white solid.

B. $N^1$-Methyl-$N^2$-(4-methylbenzimidazol-5-yl)guanidine, dihydrochloric acid salt.

To a solution of 399 mg of 5-[$N^2$,$N^3$-bis (benzyloxycarbonyl)-$N^2$-methylguanidino]-4-methylbenzimidazole in 10 mL of ethanol are added 160 mg of ammonium formate and a catalytic amount of palladium-on-carbon. The resulting suspension is heated to reflux for 5 hours. The reaction mixture is filtered on Celite and the filtrate is rotary evaporated. The residue is dissolved in 2 mL of methanol and 0.5 mL of concentrated hydrochloric acid is added. After 5 minutes, the mixture is rotary evaporated and dried under vacuum. The residue is purified by recrystallization using methanol/ethyl acetate to provide 211 mg of $N^1$-Methyl-$N^2$-(4-methylbenzimidazol-5-yl)guanidine, dihydrochloric acid salt as a solid.

Example 7

8-(Methylquinolin-7-yl)guanidine
A. 8-Methyl-7-nitroquinoline.

To a suspension of 2 g of 2-methyl-3-nitroaniline and 1.02 g of arsenic(v) oxide hydrate are added 2.88 mL of glycerin followed by 1.09 mL of concentrated sulfuric acid. The resulting black slurry is stirred at about 150° C. for 4 hours. The black oil is cooled to room temperature, diluted with water and poured into a mixture of 25% aqueous ammonium hydroxide and ethyl acetate. The organic layer is washed with water followed by brine. The aqueous layers are extracted with ethyl acetate; the combined organic layers are dried over magnesium sulfate, filtered and rotary evaporated. The residue is purified by flash column chromatography on silica gel, eluting with 50% ethyl acetate/hexanes followed by recrystallization from hexanes/methylene chloride to provide 1.45 g of 8-methyl-7-nitroquinoline as a pale brown solid.

B. 7-Amino-8-methylguinoline.

To a solution of 1.45 g of 8-methyl-7-nitroquinoline in 20 mL of ethanol are added 1.45 g of ammonium formate and a catalytic amount of palladium-on-carbon. The resulting suspension is stirred at room temperature for 3 hours. The reaction mixture is filtered on Celite and the filtrate is rotary evaporated. The residue is purified by flash column chromatography on silica gel, eluting with 50% ethyl acetate/hexanes followed by recrystallization from hexanes/methylene chloride to provide 1.10 g of 7-amino-8-methylquinoline as a pale yellow solid.

C. 7-[$N^2$,$N^3$-Bis(benzyloxycarbonyl)guanidino]-8-methylquinoline.

To a pale yellow solution of 500 mg of 7-amino-8-methylquinoline in 20 mL of tetrahydrofuran are added 1.18 g of ethyl N,N-bis(benzyloxy-carbonyl)pseudothiourea and 1.01 g of mercuric acetate and the mixture is stirred at room temperature for 1 hour. The suspension is diluted with ethyl acetate and the organic layer is washed with water followed by brine. The aqueous layers are extracted with ethyl acetate; the combined organic layers are dried over magnesium sulfate, filtered and rotary evaporated. The residue is purified by flash column chromatography on silica gel, eluting with 50% ethyl acetate/hexanes and recrystallization from hexanes/methylene chloride to provide 1.257 g of 7-[$N^2$,$N^3$-bis(benzyloxycarbonyl)guanidino]-8-methylquinoline as a white solid.

D. 8-(Methylquinolin-7-yl)guanidine, dihydrochloric acid salt.

To a solution of 1.25 g of 7-[$N^2$,$N^3$-bis (benzyloxycarbonyl)guanidino]-8-methylquinoline in 40 mL of ethanol are added 672 mg of ammonium formate and a catalytic amount of palladium-on-carbon. The resulting suspension is stirred at room temperature for 10 hours. The reaction mixture is filtered on Celite and the filtrate is rotary evaporated. The residue is dissolved in 25 mL of methanol and treated with a slow stream of hydrogen chloride gas for about 5 minutes. The resulting solution is stirred at room temperature for 2 hours and rotary evaporated to give a pale yellow solid that is purified by recrystallization from methanol/ethyl acetate to provide 313 mg of 8-(methylquinolin-7-yl)guanidine, dihydrochloric acid salt as a yellow solid.

Example 8

(8-Bromoguinolin-7-yl)guanidine
A. 7-Amino-8-bromoguinoline.

To a solution of 401 mg of 7-aminoquinoline in 15 mL of glacial acetic acid are added 913 mg of sodium acetate followed by a solution of 0.14 mL of bromine in 15 mL of glacial acetic acid. The resulting yellow slurry is stirred at room temperature for 2 hours. The brown mixture is rotary evaporated and the residue is diluted with water and ethyl acetate. The mixture is basified using 1 N sodium hydroxide and decanted. The organic layer is washed with water followed by brine. The combined aqueous layers are extracted with ethyl acetate; the combined organic layers are dried over magnesium sulfate and rotary evaporated. The residue is purified by flash column chromatography on silica gel, eluting with 20% to 50% ethyl acetate/hexanes followed by recrystallization from hexanes/methylene chloride to provide 521 mg of 7-amino-8-bromoquinoline as a pale brown solid.

B. 7-[$N^2$,$N^3$-Bis(tert-butoxycarbonyl)guanidino]-8-bromoquinoline.

To a pale yellow solution of 0.40 g of 7-amino-8-bromoquinoline in 10 mL of tetrahydrofuran are added 1.11 g of ethyl N,N-bis(tert-butoxy carbonyl)pseudothiourea and 1.16 g of mercuric acetate and the mixture is stirred at room temperature for 26 hours. The suspension is diluted with ethyl acetate and washed with water followed by brine. The aqueous layers are extracted with ethyl acetate; the combined organic layers are dried over magnesium sulfate and rotary evaporated. The residue is purified by flash column chromatography on silica gel, eluting with 15% ethyl acetate/hexanes to provide 0.78 g of 7-[$N^2$,$N^3$-bis(tert-butoxycarbonyl)guanidino]-8-bromoquinoline as a white solid.

C. (8-Bromoquinolin-7-yl)guanidine, hydrochloric acid salt.

To a cold (0° C.) solution of 0.735 g of 7-[$N^2$,$N^3$-bis(tert-butoxy-carbonyl)guanidino]-8-bromoquinoline in 2 mL of methylene chloride are added 2 mL of trifluoroacetic acid. The resulting solution is stirred at room temperature for 3 hours and rotary evaporated to a viscous oil. The oil is dissolved in 10 mL of methanol and 0.5 mL of concentrated hydrochloric acid is added. After 5 minutes, the solution is rotary evaporated and dried under vacuum. The solid residue is recrystallized from methanol/ethyl acetate to provide 0.41 g of (8-bromoquinolin-7-yl)guanidine, hydrochloric acid salt as a yellow solid.

Example 9

(6-Methylbenzothiazol-5-yl)guanidine

A. 6-Methyl-5-nitrobenzothiazole.

A mixture of 1.6 g of 5-chloro-2,4-dinitrotoluene and 20 mL of N,N-dimethyl-thioformamide is heated to 120° C. for 16 hours. After cooling to room temperature, the mixture is purified by flash column chromatography on silica gel, eluting with 3% to 10% ethyl acetate/hexanes to provide 0.78 g of 6-methyl-5-nitrobenzothiazole as a yellow solid.

B. 5-Amino-6-methylbenzothiazole.

A mixture of 0.78 g of 6-methyl-5-nitrobenzothiazole and 3.62 g of stannous chloride dihydrate in 25 mL of ethanol is heated to 65° C. for 4 hours. The cooled reaction mixture is poured into 10 mL of 50% sodium hydroxide and 45 mL of brine and extracted with ether (4×35 mL). The combined organic layers are washed with brine, dried over sodium sulfate and rotary evaporated. The residue is purified by flash column chromatography on silica gel, eluting with 15% ethyl acetate/hexanes to provide 0.45 g of 5-amino-6-methylbenzothiazole as a yellow solid.

C. 5-[$N^2$,$N^3$-Bis(benzyloxycarbonyl)quanidino]-6-methylbenzothiazole.

To a solution of 230 mg of 5-amino-6-methylbenzothiazole in 10 mL of 1/1 ethyl acetate/methanol are added 520 mg of ethyl N,N-bis(benzyloxycarbonyl)-pseudothiourea and 450 mg of mercuric acetate and the mixture is stirred at room temperature for 24 hours.

The mixture is filtered on Celite and rotary evaporated. The residue is purified by flash column chromatography on silica gel, eluting with 20% ethyl acetate/hexanes to provide 598 mg of 5-[$N^2$,$N^3$-bis(benzyloxycarbonyl)guanidino]-6-methylbenzothiazole as a yellow solid.

D. (6-Methylbenzothiazol-5-yl)quanidine, trihydrobromic acid salt.

To a solution of 0.58 g of 5-[$N^2$,$N^3$-bis(benzyloxycarbonyl)guanidino]-6-methylbenzothiazole in 25 mL of 1/1 methanol/ethyl acetate is added 1 g of 10% palladium-on-carbon. The mixture is stirred under hydrogen at atmospheric pressure for 3 days. The mixture is filtered on Celite and rotary evaporated. The residue is dissolved into a minimum amount of ethanol and is treated with 0.6 mL of 30% hydrobromic acid/acetic acid. Ethyl acetate is added dropwise to the point of cloudiness and the mixture is stored in the freezer until crystallization occurs. The solid is filtered and dried under vacuum to provide 96 mg of (6-methylbenzothiazol-5-yl)guanidine, trihydrobromic acid salt as a white solid.

Example 10

(4-Bromobenzothiazol-5-yl)guanidine

A. 5-Nitrobenzothiazole.

A mixture of 10 g of 1-chloro-2,4-dinitrobenzene and 20.26 g of N,N-dimethylthioformamide is heated to 60° C. for 3 hours. The resulting solid is suspended in 25 mL of xylene and the mixture is heated to reflux for 4 hours. The mixture is allowed to cool to room temperature and 15 mL of ethanol are added. The resulting suspension is filtered, and the brown solid is washed with a minimum amount of ethanol. The solid is dissolved in 120 mL of ethanol, heated to boiling, and filtered hot to remove trace solids. After reduction of the volume to about 100 mL, the solution is allowed to stand overnight at room temperature. The resulting solid is filtered and washed with ethanol to provide 4.68 g of 5-nitrobenzothiazole as reddish-brown needles.

B. 5-Aminobenzothiazole.

A mixture of 3.46 g of 5-nitrobenzothiazole and 15.7 g of stannous chloride dihydrate in 55 mL of 2-propanol is heated to reflux for 3 hours. The cooled reaction mixture is poured into 150 mL of ice/water and neutralized to pH 7 using solid sodium hydroxide. The mixture is extracted with ethyl acetate (3×50 mL). The combined organic layers are dried over sodium sulfate, filtered through a short pad of silica gel, and rotary evaporated to provide 2.45 g of 5-aminobenzothiazole as a yellow-brown solid.

C. 5-Amino-4-bromobenzothiazole.

To a cooled (5° C.) solution of 2.04 g of 5-aminobenzothiazole in 60 mL of chloroform are added dropwise 2.15 g of bromine while maintaining the temperature below 10° C. After completion of the addition, the reaction mixture is stirred for 30 minutes at room temperature, then diluted with 14 mL of concentrated ammonium hydroxide and 16 mL of methylene chloride. The aqueous layer is washed with methylene chloride (2×16 mL) and the combined organic layers are rotary evaporated. The residue is purified by an aspirator vacuum-filtration through silica gel, eluting with 15% to 30 ethyl acetate in hexanes to provide 2.44 g of 5-amino-4-bromobenzothiazole as a reddish solid.

D. (4-Bromobenzothiazol-5-yl)quanidine, hydrochloric acid salt.

A mixture of 100 mg of 5-amino4-bromobenzothiazole, 0.05 mL of water and 0.097 mL of concentrated hydrochloric acid is stirred at room temperature for 5 minutes. To this mixture are added 74 mg of cyanamide and the new mixture is stirred for 90 minutes at 70° C. The reaction mixture is cooled to 0° C. and 0.194 mL of water and 0.098 mL of concentrated hydrochloric acid are added. The mixture is stirred for 30 minutes at 0° C. and rotary evaporated. The residue is diluted with 1 mL of methanol and precipitated with ether to provide 41 mg of (4-bromobenzothiazol-5-yl)guanidine, hydrochloric acid salt as a white solid.

Example 11

N,N'-Dimethyl-(8-methylquinolin-7-yl)Guanidine

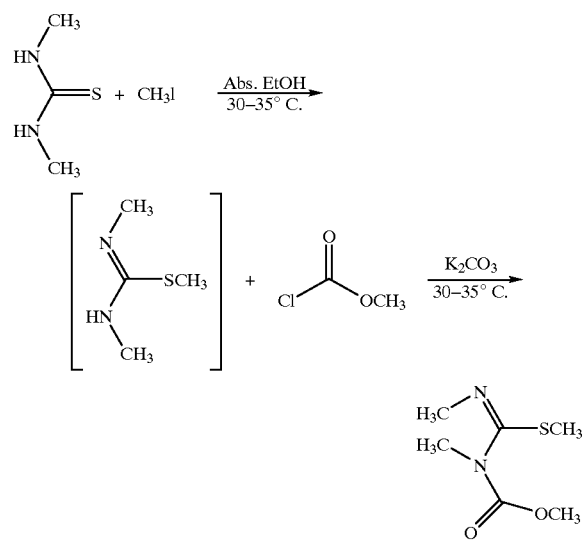

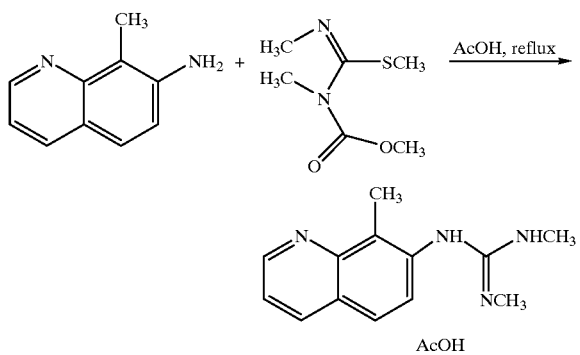

A. Methyl N,N'-dimethylthiopseudourea.

N,N'-Dimethylthioguanidine (5.0 g) is added to absolute ethanol (40 mL) while stirring. Methyl iodide (4.3 ml, 1.4 Eq) is rapidly added. The reaction mixture is warmed to 30–35° C. for 45 minutes. This solution is used directly in the next reaction.

B. Methyl N-carbomethoxy-N,N'-dimethylthiopseudourea.

Potassium carbonate (10.1 g) is added to the mixture in (A) above, followed by addition of methyl chloroformate (4.2 mL) while stirring. After 45 minutes, the reaction mixture is heated to 55° C. and the insoluble salts are filtered off. These salts are washed with 10 mL of absolute ethanol. The filtrate (and ethanol wash) is cooled to −20° C. and the recrystallized product is isolated on a Buchner funnel. The product is washed with 10 mL cold (−20° C.) absolute ethanol. The product is dried overnight under vacuum at room temperature, yielding methyl N-carbomethoxy-N,N'-dimethylthiopseudourea.

C. N,N'-Dimethyl-(8-methylquinolin-7-yl)guanidine.

The methyl N-carbomethoxy-N,N'-dimethylthiopseudourea is combined with 8-methyl-7-nitroquinoline, as prepared in Example 7B, in 10% acetic acid in ethanol and heated to reflux. After the starting amine is consumed, the mixture is decolorized with carbon. The mixture is cooled, filtered and rotary evaporated. Upon recrystallization and drying, N,N'-dimethyl-(8-methylquinolin-7-yl)guanidine is obtained as an acetic acid salt.

Using the methodologies outlined and exemplified above the following compounds are made. In these examples where $R_1$ is nil, (a) is a double bond, and guanidinyl is signified by GNDNL;

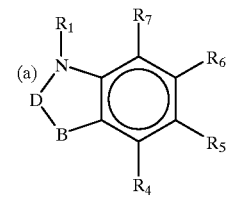

| Example | $R_1$ | D | B | $R_4$ | $R_5$ | $R_6$ | $R_7$ |
|---|---|---|---|---|---|---|---|
| In the following table, $R_{10} = R_{11} =$ hydrogen. | | | | | | | |
| 12 | nil | CH | NH | Cl | H | GNDNL | Me |
| 13 | nil | CH | NH | Br | H | GNDNL | Me |
| 14 | nil | CH | NH | I | H | GNDNL | Me |
| 15 | nil | CH | NH | F | H | GNDNL | Me |
| 16 | nil | CH | NH | OMe | H | GNDNL | Me |
| 17 | nil | CH | NH | CN | H | GNDNL | Me |
| 18 | nil | CH | NH | Cl | H | GNDNL | Br |
| 19 | nil | CH | NH | Br | H | GNDNL | Br |
| 20 | nil | CH | NH | I | H | GNDNL | Br |
| 21 | nil | CH | NH | F | H | GNDNL | Br |
| 22 | nil | CH | NH | OMe | H | GNDNL | Br |
| 23 | nil | CH | NH | Me | H | GNDNL | Br |
| 24 | nil | CH | NH | CN | H | GNDNL | Br |
| 25 | nil | CH | NH | Cl | H | GNDNL | Cl |
| 26 | nil | CH | NH | Br | H | GNDNL | Cl |
| 27 | nil | CH | NH | I | H | GNDNL | Cl |
| 28 | nil | CH | NH | F | H | GNDNL | Cl |
| 29 | nil | CH | NH | OMe | H | GNDNL | Cl |
| 30 | nil | CH | NH | Me | H | GNDNL | Cl |
| 31 | nil | CH | NH | CN | H | GNDNL | Cl |
| 32 | nil | CH | NH | H | H | GNDNL | Cl |
| 33 | nil | CH | NH | Cl | H | GNDNL | OMe |
| 34 | nil | CH | NH | Br | H | GNDNL | OMe |
| 35 | nil | CH | NH | I | H | GNDNL | OMe |
| 36 | nil | CH | NH | F | H | GNDNL | OMe |
| 37 | nil | CH | NH | OMe | H | GNDNL | OMe |
| 38 | nil | CH | NH | Me | H | GNDNL | OMe |
| 39 | nil | CH | NH | CN | H | GNDNL | OMe |
| 40 | nil | CH | NH | H | H | GNDNL | OMe |
| 41 | nil | CH | NH | Cl | H | GNDNL | SMe |
| 42 | nil | CH | NH | Br | H | GNDNL | SMe |
| 43 | nil | CH | NH | I | H | GNDNL | SMe |
| 44 | nil | CH | NH | F | H | GNDNL | SMe |
| 45 | nil | CH | NH | OMe | H | GNDNL | SMe |
| 46 | nil | CH | NH | Me | H | GNDNL | SMe |
| 47 | nil | CH | NH | CN | H | GNDNL | SMe |
| 48 | nil | CH | NH | H | H | GNDNL | SMe |

-continued

| Example | $R_1$ | D | B | $R_4$ | $R_5$ | $R_6$ | $R_7$ |
|---|---|---|---|---|---|---|---|
| 49 | nil | CHMe | NH | H | H | GNDNL | Et |
| 50 | nil | CHMe | NH | H | H | GNDNL | OMe |
| 51 | nil | CH | S | H | H | GNDNL | Me |
| 52 | nil | CH | S | Me | H | GNDNL | Me |
| 53 | nil | CH | S | OMe | H | GNDNL | Me |
| 54 | nil | CH | S | Br | H | GNDNL | Me |
| 55 | nil | CH | S | Cl | H | GNDNL | Me |
| 56 | nil | CH | S | F | H | GNDNL | Me |
| 57 | nil | CH | S | I | H | GNDNL | Me |
| 58 | nil | CH | S | CN | H | GNDNL | Me |
| 59 | nil | CH | S | Me | H | GNDNL | Br |
| 60 | nil | CH | S | OMe | H | GNDNL | Br |
| 61 | nil | CH | S | Br | H | GNDNL | Br |
| 62 | nil | CH | S | Cl | H | GNDNL | Br |
| 63 | nil | CH | S | F | H | GNDNL | Br |
| 64 | nil | CH | S | I | H | GNDNL | Br |
| 65 | nil | CH | S | CN | H | GNDNL | Br |
| 66 | nil | CH | S | H | OMe | GNDNL | H |
| 67 | nil | CH | S | H | Br | GNDNL | H |
| 68 | nil | CH | S | H | Me | GNDNL | Me |
| 69 | nil | CH | S | H | OMe | GNDNL | Me |
| 70 | nil | CH | S | H | Br | GNDNL | Me |
| 71 | nil | CH | S | H | Me | GNDNL | Et |
| 72 | nil | CH | S | H | OMe | GNDNL | Et |
| 73 | nil | CH | S | H | Br | GNDNL | Et |
| 74 | nil | CH | S | H | Me | GNDNL | Br |
| 75 | nil | CH | S | H | OMe | GNDNL | Br |
| 76 | nil | CH | S | H | Br | GNDNL | Br |
| 77 | nil | CH | S | H | Me | GNDNL | OMe |
| 78 | nil | CH | S | H | OMe | GNDNL | OMe |
| 79 | nil | CH | S | H | Br | GNDNL | OMe |
| 80 | nil | CH | S | H | Me | GNDNL | SMe |
| 81 | nil | CH | S | H | OMe | GNDNL | SMe |
| 82 | nil | CH | S | H | Br | GNDNL | SMe |
| 83 | H | CH= | =CH | H | H | GNDNL | Me |
| 84 | H | CH= | =C(Br) | H | H | GNDNL | Me |
| 85 | H | $CH_2$ | $CH_2$ | H | H | GNDNL | Me |
| 86 | H | N= | =CH | H | H | GNDNL | Me |
| 87 | H | N= | =CH | H | H | GNDNL | Et |
| 88 | H | N= | =CH | H | H | GNDNL | Br |
| 89 | nil | CH | O | H | H | GNDNL | Me |
| 90 | nil | CH | CH=CH | Cl | H | GNDNL | Me |
| 91 | nil | CH | CH=CH | Br | H | GNDNL | Me |
| 92 | nil | CH | CH=CH | I | H | GNDNL | Me |
| 93 | nil | CH | CH=CH | F | H | GNDNL | Me |
| 94 | nil | CH | CH=CH | OMe | H | GNDNL | Me |
| 95 | nil | CH | CH=CH | Me | H | GNDNL | Me |
| 96 | nil | CH | CH=CH | CN | H | GNDNL | Me |
| 97 | nil | CH | CH=CH | Cl | H | GNDNL | Br |
| 98 | nil | CH | CH=CH | Br | H | GNDNL | Br |
| 99 | nil | CH | CH=CH | I | H | GNDNL | Br |
| 100 | nil | CH | CH=CH | F | H | GNDNL | Br |
| 101 | nil | CH | CH=CH | OMe | H | GNDNL | Br |
| 102 | nil | CH | CH=CH | Me | H | GNDNL | Br |
| 103 | nil | CH | CH=CH | CN | H | GNDNL | Br |
| 104 | nil | CH | CH=CH | Cl | H | GNDNL | Cl |
| 105 | nil | CH | CH=CH | Br | H | GNDNL | Cl |
| 106 | nil | CH | CH=CH | I | H | GNDNL | Cl |
| 107 | nil | CH | CH=CH | F | H | GNDNL | Cl |
| 108 | nil | CH | CH=CH | OMe | H | GNDNL | Cl |
| 109 | nil | CH | CH=CH | Me | H | GNDNL | Cl |
| 110 | nil | CH | CH=CH | CN | H | GNDNL | Cl |
| 111 | nil | CH | CH=CH | H | H | GNDNL | Cl |
| 112 | nil | CH | CH=CH | H | Me | GNDNL | Me |
| 113 | nil | CH | CH=CH | H | Me | GNDNL | Br |
| 114 | nil | CH | CH=CH | H | Me | GNDNL | Cl |
| 115 | nil | CH | CH=CH | H | Me | GNDNL | OMe |
| 116 | nil | CH | CH=CH | H | Me | GNDNL | SMe |
| 117 | nil | CH | CH=CH | H | OMe | GNDNL | Me |
| 118 | nil | CH | CH=CH | H | OMe | GNDNL | Br |
| 119 | nil | CH | CH=CH | H | OMe | GNDNL | Cl |
| 120 | nil | CH | CH=CH | H | OMe | GNDNL | OMe |
| 121 | nil | CH | CH=CH | H | OMe | GNDNL | SMe |
| 122 | nil | CH | CH=CH | H | SMe | GNDNL | Me |
| 123 | nil | CH | CH=CH | H | SMe | GNDNL | Br |
| 124 | nil | CH | CH=CH | H | SMe | GNDNL | Cl |
| 125 | nil | CH | CH=CH | H | SMe | GNDNL | OMe |

-continued

| Example | R₁ | D | B | R₄ | R₅ | R₆ | R₇ |
|---|---|---|---|---|---|---|---|
| 126 | nil | CH | CH=CH | H | SMe | GNDNL | SMe |
| 127 | nil | CH | CH=CH | H | Br | GNDNL | Me |
| 128 | nil | CH | CH=CH | H | Br | GNDNL | Br |
| 129 | nil | CH | CH=CH | H | Br | GNDNL | Cl |
| 130 | nil | CH | CH=CH | H | Br | GNDNL | OMe |
| 131 | nil | CH | CH=CH | H | Br | GNDNL | SMe |
| 132 | nil | CH | CH=CH | H | Cl | GNDNL | Me |
| 133 | nil | CH | CH=CH | H | Cl | GNDNL | Cl |
| 134 | nil | CH | CH=CH | Me | Me | GNDNL | Me |
| 135 | nil | CH | CH=CH | Me | Cl | GNDNL | Me |
| 136 | nil | CH | CH=CH | Me | Br | GNDNL | Me |
| 137 | nil | CH | CH=CH | Me | I | GNDNL | Me |
| 138 | nil | CH | CH=CH | Me | GNDNL | H | Cl |
| 139 | nil | CH | CH=CH | Me | GNDNL | H | Br |
| 140 | nil | CH | CH=CH | Me | GNDNL | H | I |
| 141 | nil | CH | CH=CH | Me | GNDNL | H | Me |
| 142 | nil | CH | CH=CH | Et | GNDNL | H | Cl |
| 143 | nil | CH | CH=CH | Et | GNDNL | H | Br |
| 144 | nil | CH | CH=CH | Et | GNDNL | H | I |
| 145 | nil | CH | CH=CH | Et | GNDNL | H | Me |
| 146 | nil | CH | CH=CH | Br | GNDNL | H | Cl |
| 147 | nil | CH | CH=CH | Br | GNDNL | H | Br |
| 148 | nil | CH | CH=CH | Br | GNDNL | H | I |
| 149 | nil | CH | CH=CH | Br | GNDNL | H | Me |
| 150 | nil | CH | CH=CH | Cl | GNDNL | H | Cl |
| 151 | nil | CH | CH=CH | Cl | GNDNL | H | Br |
| 152 | nil | CH | CH=CH | Cl | GNDNL | H | I |
| 153 | nil | CH | CH=CH | Cl | GNDNL | H | Me |
| 154 | nil | CH | CH=CH | OMe | GNDNL | H | Cl |
| 155 | nil | CH | CH=CH | OMe | GNDNL | H | Br |
| 156 | nil | CH | CH=CH | OMe | GNDNL | H | I |
| 157 | nil | CH | CH=CH | OMe | GNDNL | H | Me |
| 158 | nil | CH | CH=CH | SMe | GNDNL | H | Cl |
| 159 | nil | CH | CH=CH | SMe | GNDNL | H | Br |
| 160 | nil | CH | CH=CH | SMe | GNDNL | H | I |
| 161 | nil | CH | CH=CH | SMe | GNDNL | H | Me |
| 162 | nil | CH | CH=CH | Me | GNDNL | Me | H |
| 163 | nil | CH | CH=CH | Me | GNDNL | Br | H |
| 164 | nil | CH | CH=CH | Me | GNDNL | Cl | H |
| 165 | nil | CH | CH=CH | Me | GNDNL | OMe | H |
| 166 | nil | CH | CH=CH | Me | GNDNL | SMe | H |
| 167 | nil | CH | CH=CH | Et | GNDNL | Me | H |
| 168 | nil | CH | CH=CH | Et | GNDNL | Br | H |
| 169 | nil | CH | CH=CH | Et | GNDNL | Cl | H |
| 170 | nil | CH | CH=CH | Et | GNDNL | OMe | H |
| 171 | nil | CH | CH=CH | Et | GNDNL | SMe | H |
| 172 | nil | CH | CH=CH | Br | GNDNL | Me | H |
| 173 | nil | CH | CH=CH | Br | GNDNL | Br | H |
| 174 | nil | CH | CH=CH | Br | GNDNL | Cl | H |
| 175 | nil | CH | CH=CH | Br | GNDNL | OMe | H |
| 176 | nil | CH | CH=CH | Br | GNDNL | SMe | H |
| 177 | nil | CH | CH=CH | Cl | GNDNL | Me | H |
| 178 | nil | CH | CH=CH | Cl | GNDNL | Br | H |
| 179 | nil | CH | CH=CH | Cl | GNDNL | Cl | H |
| 180 | nil | CH | CH=CH | Cl | GNDNL | OMe | H |
| 181 | nil | CH | CH=CH | Cl | GNDNL | SMe | H |
| 182 | nil | CH | CH=CH | OMe | GNDNL | Me | H |
| 183 | nil | CH | CH=CH | OMe | GNDNL | Br | H |
| 184 | nil | CH | CH=CH | OMe | GNDNL | Cl | H |
| 185 | nil | CH | CH=CH | OMe | GNDNL | OMe | H |
| 186 | nil | CH | CH=CH | OMe | GNDNL | SMe | H |
| 187 | nil | CH | CH=CH | SMe | GNDNL | Me | H |
| 188 | nil | CH | CH=CH | SMe | GNDNL | Br | H |
| 189 | nil | CH | CH=CH | SMe | GNDNL | OMe | H |
| 190 | nil | CH | CH=CH | SMe | GNDNL | SMe | H |
| 191 | nil | CH | CH=CH | Me | GNDNL | Me | Me |
| 192 | nil | CH | C(Me)=CH | Me | GNDNL | H | Me |
| 193 | nil | CH | C(Br)=CH | Me | GNDNL | H | Me |
| 194 | nil | CH | C(Cl)=CH | Me | GNDNL | H | Me |
| 195 | nil | CH | C(F)=CH | Me | GNDNL | H | Me |
| 196 | nil | CH | CH=C(Me) | Me | GNDNL | H | Me |
| 197 | nil | CH | CH=C(CN) | Me | GNDNL | H | Me |
| 198 | nil | CH | CH=C(Br) | Me | GNDNL | H | Me |
| 199 | nil | CH | CH=C(Cl) | Me | GNDNL | H | Me |
| 200 | nil | CH | CH=C(F) | Me | GNDNL | H | Me |
| 201 | nil | CH | S | Me | GNDNL | H | Me |
| 202 | nil | CH | S | Me | GNDNL | H | Cl |

-continued

| Example | $R_1$ | D | B | $R_4$ | $R_5$ | $R_6$ | $R_7$ |
|---|---|---|---|---|---|---|---|
| 203 | nil | CH | S | Me | GNDNL | H | Br |
| 204 | nil | CH | S | Me | GNDNL | H | I |
| 205 | nil | CH | S | Me | GNDNL | H | OMe |
| 206 | nil | CH | S | Cl | GNDNL | H | Me |
| 207 | nil | CH | S | Cl | GNDNL | H | Cl |
| 208 | nil | CH | S | Cl | GNDNL | H | Br |
| 209 | nil | CH | S | Cl | GNDNL | H | I |
| 210 | nil | CH | S | Cl | GNDNL | H | OMe |
| 211 | nil | CH | S | Br | GNDNL | H | Me |
| 212 | nil | CH | S | Br | GNDNL | H | Cl |
| 213 | nil | CH | S | Br | GNDNL | H | Br |
| 214 | nil | CH | S | Br | GNDNL | H | I |
| 215 | nil | CH | S | Br | GNDNL | H | OMe |
| 216 | nil | CH | S | I | GNDNL | H | Me |
| 217 | nil | CH | S | I | GNDNL | H | Cl |
| 218 | nil | CH | S | I | GNDNL | H | Br |
| 219 | nil | CH | S | I | GNDNL | H | I |
| 220 | nil | CH | S | I | GNDNL | H | OMe |
| 221 | nil | CH | S | Et | GNDNL | H | Me |
| 222 | nil | CH | S | Et | GNDNL | H | Cl |
| 223 | nil | CH | S | Et | GNDNL | H | Br |
| 224 | nil | CH | S | Et | GNDNL | H | I |
| 225 | nil | CH | S | Et | GNDNL | H | OMe |
| 226 | nil | CH | S | Me | GNDNL | Me | H |
| 227 | nil | CH | S | Me | GNDNL | Cl | H |
| 228 | nil | CH | S | Me | GNDNL | Br | H |
| 229 | nil | CH | S | Me | GNDNL | I | H |
| 230 | nil | CH | S | Cl | GNDNL | Cl | H |
| 231 | nil | CH | S | Me | GNDNL | Me | Me |
| 232 | nil | CH | S | Me | GNDNL | Cl | Me |
| 233 | nil | CH | S | Me | GNDNL | Br | Me |
| 234 | nil | CH | S | Me | GNDNL | I | Me |
| 235 | nil | CH | S | Et | GNDNL | H | Me |
| 236 | nil | CH | S | Et | GNDNL | H | Me |
| In the following table, $R_{10}$ = Me and $R_{11}$ = H. | | | | | | | |
| 237 | nil | CH | NH | H | H | GNDNL | Br |
| 238 | nil | CH | CH=CH | H | H | GNDNL | Me |
| 239 | nil | CH | CH=CH | Me | GNDNL | H | Me |
| 240 | nil | CH | S | H | H | GNDNL | Me |
| 241 | nil | CH | S | H | H | GNDNL | Br |
| In the following table, $R_{10}$ = Et and $R_{11}$ = H. | | | | | | | |
| 242 | nil | CH | N | H | H | GNDNL | Me |
| 243 | nil | CH | CH=CH | H | H | GNDNL | Me |
| 244 | nil | CH | CH=CH | Me | GNDNL | H | Me |
| 245 | nil | CH | S | H | H | GNDNL | Me |
| 246 | nil | CH | S | H | H | GNDNL | Br |

Compositions

Another aspect of this invention is compositions which comprise a safe and effective amount of a subject compound, or a pharmaceutically-acceptable salt thereof, and a pharmaceutically-acceptable carrier.

As used herein, "safe and effective amount" means an amount of the subject compound sufficient to significantly induce a positive modification in the condition to be treated, but low enough to avoid serious side effects (at a reasonable benefit/risk ratio), within the scope of sound medical judgment. A safe and effective amount of the subject compound will vary with the age and physical condition of the patient being treated, the severity of the condition, the duration of the treatment, the nature of concurrent therapy, the particular pharmaceutically-acceptable carrier utilized, and like factors within the knowledge and expertise of the attending physician.

Preparing a dosage form is within the purview of the skilled artisan. Examples are provided for the skilled artisan, but are non-limiting, and it is contemplated that the skilled artisan can prepare variations of the compositions claimed.

Compositions of this invention preferably comprise from about 0.0001% to about 99% by weight of the subject compound, more preferably from about 0.01% to about 90% of the compound of the invention. Depending upon the route of administration and attendant bioavailability, solubility or dissolution characteristics of the dosage form, the dosage form has preferably from about 10% to about 50%, also preferably from about 5% to about 10%, also preferably from about 1% to about 5%, and also preferably from about 0.01% to about 1% of the subject compound. The frequency of dosing of the subject compound is dependent upon the pharmacokinetic properties of each specific agent (for example, biological half-life) and can be determined by the skilled artisan.

In addition to the subject compound, the compositions of this invention contain a pharmaceutically-acceptable carrier. The term "pharmaceutically-acceptable carrier", as used herein, means one or more compatible solid or liquid filler diluents or encapsulating substances which are suitable for administration to a mammal. The term "compatible", as used herein, means that the components of the composition are capable of being commingled with the subject compound, and with each other, in a manner such that there is no interaction which would substantially reduce the pharmaceutical efficacy of the composition under ordinary use situations. Preferably when liquid dose forms are used, the compounds of the invention are soluble in the components of the composition. Pharmaceutically-acceptable carriers must, of course, be of sufficiently high purity and sufficiently low toxicity to render them suitable for administration to the mammal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the subject compound is basically determined by the way the compound is to be administered. If the subject compound is to be injected, the preferred pharmaceutically-acceptable carrier is sterile, physiological saline, with a blood-compatible suspending agent, the pH of which has been adjusted to about 7.4.

If the preferred mode of administering the subject compound is perorally, the preferred unit dosage form is therefore tablets, capsules, lozenges, chewable tablets, and the like. Such unit dosage forms comprise a safe and effective amount of the subject compound, which is preferably from about 0.01 mg to about 350 mg, more preferably from about 0.1 mg to about 35 mg, based on a 70 kg person. The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of this invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.001% to about 5% of the subject compound, more preferably from about 0.01% to about 0.5%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Compositions can also be used to deliver the compound to the site where activity is desired: intranasal doses for nasal decongestion, inhalants for asthma, and eye drops, gels and creams for ocular disorders.

Preferred compositions of this invention include solutions or emulsions, preferably aqueous solutions or emulsions comprising a safe and effective amount of a subject compound intended for topical intranasal administration. Such compositions preferably comprise from about 0.001% to about 25% of a subject compound, more preferably from about 0.01% to about 10%. Similar compositions are preferred for systemic delivery of subject compounds by the intranasal route. Compositions intended to deliver the compound systemically by intranasal dosing preferably comprise similar amounts of a subject compound as are determined to be safe and effective by peroral or parenteral administration. Such compositions used for intranasal dosing also typically include safe and effective amounts of preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfate and others; aromatic agents; viscosity adjustors, such as polymers, including cellulose and derivatives thereof, and polyvinyl alcohol and acids and bases to adjust the pH of these aqueous compositions as needed. The compositions may also comprise local anesthetics or other actives. These compositions can be used as sprays, mists, drops, and the like.

Other preferred compositions of this invention include aqueous solutions, suspensions, and dry powders comprising a safe and effective amount of a subject compound intended for atomization and inhalation administration. Such compositions preferably comprise from about 0.1% to about 50% of a subject compound, more preferably from about 1% to about 20%; of course, the amount can be altered to fit the circumstance of the patient contemplated and the package. Such compositions are typically contained in a container with attached atomizing means. Such compositions also typically include propellants such as chlorofluorocarbons 12/11 and 12/114, and more environmentally friendly fluorocarbons, or other nontoxic volatiles; solvents such as water, glycerol and ethanol, these include cosolvents as needed to solvate or suspend the active; stabilizers such as ascorbic acid, sodium metabisulfite; preservatives such as cetylpyridinium chloride and benzalkonium chloride; tonicity adjustors such as sodium chloride; buffers; and flavoring agents such as sodium saccharin. Such compositions are useful for treating respiratory disorders, such as asthma and the like.

Other preferred compositions of this invention include aqueous solutions comprising a safe and effective amount of a subject compound intended for topical intraocular administration. Such compositions preferably comprise from about 0.0001% to about 5% of a subject compound, more preferably from about 0.01% to about 0.5%. Such compositions also typically include one or more of preservatives, such as benzalkonium chloride, thimerosal, phenylmercuric acetate; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases may be used to adjust the pH of these formulations as needed.

Other preferred compositions of this invention useful for peroral administration include solids, such as tablets and capsules, and liquids, such as solutions, suspensions and emulsions (preferably in soft gelatin capsules), comprising a safe and effective amount of a subject compound. Such compositions preferably comprise from about 0.01 mg to about 350 mg per dose, more preferably from about 0.1 mg to about 35 mg per dose. Such compositions can be coated by conventional methods, typically with pH or time-dependent coatings, such that the subject compound is released in the gastrointestinal tract at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit® coatings, waxes and shellac.

Any of the compositions of this invention may optionally include other drug actives. Non-limiting examples of drug actives which may be incorporated in these compositions, include:

Antihistamines, including:

Hydroxyzine, preferably at a dosage range of from about 25 to about 400 mg; Doxylamine, preferably at a dosage range of from about 3 to about 75 mg; Pyrilamine, preferably at a dosage range of from about 6.25 to about 200 mg; Chlorpheniramine, preferably at a dosage range of from about 1 to about 24 mg; Phenindamine, preferably at a dosage range of from about 6.25 to about 150 mg; Dexchlorpheniramine, preferably at a dosage range of from about 0.5 to about 12 mg; Dexbrompheniramine, preferably at a dosage range of from about 0.5 to about 12 mg; Clemastine, preferably at a dosage range of from about 1 to about 9 mg; Diphenhydramine, preferably at a dosage range of from about 6.25 to about 300 mg; Azelastine, preferably at a dosage range of from about 140 to about 1,680 pg (when dosed intranasally); 1 to about 8 mg (when dosed orally); Acrivastine, preferably at a dosage range of from about 1 to about 24 mg; Levocarbastine (which can be dosed as an intranasal or ocular medicament), preferably at a dosage range of from about 100 to about 800 mg; Mequitazine, preferably at a dosage range of from about 5 to about 20 mg; Astemizole, preferably at a dosage range of from about 5 to about 20 mg; Ebastine, preferably at a dosage range of from about 5 to about 20 mg; Loratadine, preferably at a dosage range of from about 5 to about 40 mg; Cetirizine, preferably at a dosage range of from about 5 to about 20 mg; Terfenadine, preferably at a dosage range of from about 30 to about 480 mg; Terfenadine metabolites; Promethazine, preferably at a dosage range of from about 6.25 to about 50 mg; Dimenhydrinate, preferably at a dosage range of from about 12.5 to about 400 mg; Meclizine, preferably at a dosage range of from about 6.25 to about 50 mg; Tripelennamine, preferably at a dosage range of from about 6.25 to about 300 mg; Carbinoxamine, preferably at a dosage range of from about 0.5 to about 16 mg; Cyproheptadine, preferably at a dosage range of from about 2 to about 20 mg; Azatadine, preferably at a dosage range of from about 0.25 to about 2 mg; Brompheniramine, preferably at a dosage range of from about 1 to about 24 mg; Triprolidine, preferably at a dosage range of from about 0.25 to about 10 mg; Cyclizine, preferably at a dosage range of from about 12.5 to about 200 mg; Thonzylamine, preferably at a dosage range of from about 12.5 to about 600 mg; Pheniramine, preferably at a dosage range of from about 3 to about 75 mg; Cyclizine, preferably at a dosage range of from about 12.5 to about 200 mg and others;

Antitussives, including:

Codeine, preferably at a dosage range of from about 2.5 to about 120 mg; Hydrocodone, preferably at a dosage range of from about 2.5 to about 40 mg; Dextromethorphan, preferably at a dosage range of from about 2.5 to about 120 mg; Noscapine, preferably at a dosage range of from about 3 to about 180 mg; Benzonatate, preferably at a dosage range of from about 100 to about 600 mg; Diphenhydramine, preferably at a dosage range of from about 12.5 to about 150 mg; Chlophedianol, preferably at a dosage range of from about 12.5 to about 100 mg; Clobutinol, preferably at a dosage range of from about 20 to about 240 mg; Fominoben, preferably at a dosage range of from about 80 to about 480 mg; Glaucine; Pholcodine, preferably at a dosage range of from about 1 to about 40 mg; Zipeprol, preferably at a dosage range of from about 75 to about 300 mg; Hydromorphone, preferably at a dosage range of from about 0.5 to about 8 mg; Carbetapentane, preferably at a dosage range of from about 15 to about 240 mg; Caramiphen, preferably at a dosage range of from about 10 to about 100 mg; Levopropoxyphene, preferably at a dosage range of from about 25 to about 200 mg and others;

Antiinflammatories, preferably Non-Steroidal Anti-inflammatories, (NSAIDS) including;

Ibuprofen, preferably at a dosage range of from about 50 to about 3,200 mg; Naproxen, preferably at a dosage range of from about 62.5 to about 1,500 mg; Sodium naproxen, preferably at a dosage range of from about 110 to about 1,650 mg; Ketoprofen, preferably at a dosage range of from about 25 to about 300 mg; Indoprofen, preferably at a dosage range of from about 25 to about 200 mg; Indomethacin, preferably at a dosage range of from about 25 to about 200 mg; Sulindac, preferably at a dosage range of from about 75 to about 400 mg; Diflunisal, preferably at a dosage range of from about 125 to about 1,500 mg; Ketorolac, preferably at a dosage range of from about 10 to about 120 mg; Piroxicam, preferably at a dosage range of from about 10 to about 40 mg; Aspirin, preferably at a dosage range of from about 80 to about 4,000 mg; Meclofenamate, preferably at a dosage range of from about 25 to about 400 mg; Benzydamine, preferably at a dosage range of from about 25 to about 200 mg; Carprofen, preferably at a dosage range of from about 75 to about 300 mg; Diclofenac, preferably at a dosage range of from about 25 to about 200 mg; Etodolac, preferably at a dosage range of from about 200 to about 1,200 mg; Fenbufen, preferably at a dosage range of from about 300 to about 900 mg; Fenoprofen, preferably at a dosage range of from about 200 to about 3,200 mg; Flurbiprofen, preferably at a dosage range of from about 50 to about 300 mg; Mefenamic acid, preferably at a dosage range of from about 250 to about 1,500 mg; Nabumetone, preferably at a dosage range of from about 250 to about 2,000 mg; Phenylbutazone, preferably at a dosage range of from about 100 to about 400 mg; Pirprofen, preferably at a dosage range of from about 100 to about 800 mg; Tolmetin, preferably at a dosage range of from about 200 to about 1,800 mg and others;

Analgesics, including:

Acetaminophen, preferably at a dosage range of from about 80 to about 4,000 mg; and others:

Expectorants/Mucolytics, including:

Guaifenesin, preferably at a dosage range of from about 50 to about 2,400 mg; N-Acetylcysteine, preferably at a dosage range of from about 100 to about 600 mg; Ambroxol, preferably at a dosage range of from about 15 to about 120 mg; Bromhexine, preferably at a dosage range of from about 4 to about 64 mg; Terpin hydrate, preferably at a dosage range of from about 100 to about 1,200 mg; Potassium iodide, preferably at a dosage range of from about 50 to about 250 mg and others;

Anticholinergics (e.g., Atropinics), preferably intranasally or orally administered anticholinergics, including:

Ipratroprium (preferably intranasally), preferably at a dosage range of from about 42 to about 252 pg; Atropine sulfate (preferably oral), preferably at a dosage range of from about 10 to about 1,000 µg; Belladonna (preferably as an extract), preferably at a dosage range of from about 15 to about 45 mg equivalents; Scopolamine, preferably at a dosage range of from about 400 to about 3,200 pg; Scopolamine methobromide, preferably at a dosage range of from about 2.5 to about 20 mg; Homatropine methobromide, preferably at a dosage range of from about 2.5 to about 40 mg; Hyoscyamine (preferably oral), preferably at a dosage range of from about 125 to about 1,000 µg; Isopropramide (preferably oral), preferably at a dosage range of from about 5 to about 20 mg; Orphenadrine (preferably oral), preferably at a dosage range of from about 50 to about 400 mg; Benzalkonium chloride (preferably intranasally) preferably a 0.005 to about 0.1% solution and others;

Mast Cell Stabilizers, preferably intranasally, or orally administered mast cell stabilizers, including:

Cromalyn, preferably at a dosage range of from about 10 to about 60 mg; Nedocromil, preferably at a dosage range of from about 10 to about 60 mg; Oxatamide, preferably at a dosage range of from about 15 to about 120 mg; Ketotifen, preferably at a dosage range of from about 1 to about 4 mg; Lodoxamide, preferably at a dosage range of from about 100 to about 3,000 µg and others;

Leukotriene Antagonists, including Zileuton and others;

Methylxanthines, including:

Caffeine, preferably at a dosage range of from about 65 to about 600 mg; Theophylline, preferably at a dosage range of from about 25 to about 1,200 mg; Enprofylline; Pentoxifylline, preferably at a dosage range of from about 400 to about 3,600 mg; Aminophylline, preferably at a dosage range of from about 50 to about 800 mg; Dyphylline, preferably at a dosage range of from about 200 to about 1,600 mg and others;

Antioxidants or radical inhibitors, including:

Ascorbic acid, preferably at a dosage range of from about 50 to about 10,000 mg; Tocopherol, preferably at a dosage range of from about 50 to about 2,000 mg; Ethanol, preferably at a dosage range of from about 500 to about 10,000 mg and others;

Steroids, preferably intranasally administered steroids, including:

Beclomethasone, preferably at a dosage range of from about 84 to about 336 µg; Fluticasone, preferably at a dosage range of from about 50 to about 400 µg; Budesonide, preferably at a dosage range of from about 64 to about 256 µg; Mometasone, preferably at a dosage range of from about 50 to about 300 mg; Triamcinolone, preferably at a dosage range of from about 110 to about 440 µg; Dexamethasone, preferably at a dosage range of from about 168 to about 1,008 µg; Flunisolide, preferably at a dosage range of from about 50 to about 300 µg; Prednisone (preferably oral), preferably at a dosage range of from about 5 to about 60 mg; Hydrocortisone (preferably oral), preferably at a dosage range of from about 20 to about 300 mg and others;

Bronchodilators, preferably for inhalation, including:

Albuterol, preferably at a dosage range of from about 90 to about 1,080 µg; 2 to about 16 mg (if dosed orally); Epinephrine, preferably at a dosage range of from about 220 to about 1,320 µg; Ephedrine, preferably at a dosage range of from about 15 to about 240 mg (if dosed orally); 250 to about 1,000 µg (if dosed intranasally); Metaproterenol, preferably at a dosage range of from about 65 to about 780 µg or 10 to about 80 mg if dosed orally; Terbutaline, preferably at a dosage range of from about 200 to about 2,400 µg; 2.5 to about 20 mg (if dosed orally); Isoetharine, preferably at a dosage range of from about 340 to about 1,360 µg; Pirbuterol, preferably at a dosage range of from about 200 to about 2,400 µg; Bitolterol, preferably at a dosage range of from about 370 to about 2,220 µg; Fenoterol, preferably at a dosage range of from about 100 to about 1,200 µg; 2.5 to about 20 mg (if dosed orally); Rimeterol, preferably at a dosage range of from about 200 to about 1,600 µg; Ipratroprium, preferably at a dosage range of from about 18 to about 216 µg (inhalation) and others; and Antivirals, including:

Amantadine, preferably at a dosage range of from about 50 to about 200 mg; Rimantadine, preferably at a dosage range of from about 50 to about 200 mg; Enviroxime; Nonoxinols, preferably at a dosage range of from about 2 to about 20 mg (preferably an intranasal form); Acyclovir, preferably at a dosage range of from about 200 to about 2,000 mg (oral); 1 to about 10 mg (preferably an intranasal form); Alpha-Interferon, preferably at a dosage range of from about 3 to about 36 MIU; Beta-Interferon, preferably at a dosage range of from about 3 to about 36 MIU and others;

Ocular Drug actives: acetylcholinesterase inhibitors, e.g., echothiophate from about 0.03% to about 0.25% in topical solution and others; and Gastrointestinal actives: antidiarrheals, e.g., loperamide from about 0.1 mg to about 1.0 mg per dose, and bismuth subsalicylate from about 25 mg to about 300 mg per dose and others.

Of course, clearly contemplated and included in the description above are the acid or base addition salts, esters, metabolites, stereoisomers and enantiomers of these preferred combination actives, as well as their analogues of these actives that are safe and effective. It is also recognized that an active may be useful for more than one of the above uses, and these uses are clearly contemplated as well. This overlap is recognized in the art and adjusting dosages and the like to fit the indication is well within the purview of the skilled medical practitioner.

Methods of use

Without being bound by theory, it is contemplated that the primary mechanism by which alpha-2 agonists provide efficacy is by intervening in the biological cascade responsible for disorder(s) and/or manifestation(s) thereof. It may be that there is no deficit in alpha-2 adrenoceptor activity: such activity may be normal. However, administration of an alpha-2 agonist may be a useful way of rectifying a disorder, condition or manifestation thereof.

Thus as used herein, the terms "disease," "disorder" and "condition" are used interchangeably to refer to maladies related to or modulated by alpha-2 adrenoceptor activity.

As used herein, a disorder described by the terms "modulated by alpha-2 adrenoceptors," or "modulated by alpha-2 adrenoceptor activity" refers to a disorder, condition or disease where alpha-2 adrenoceptor activity is an effective means of alleviating the disorder or one or more of the biological manifestations of the disease or disorder; or interferes with one or more points in the biological cascade either leading to the disorder or responsible for the underlying disorder; or alleviates one or more symptoms of the disorder. Thus, disorders subject to "modulation" include those for which:

The lack of alpha-2 activity is a "cause" of the disorder or one or more of the biological manifestations, whether the activity was altered genetically, by infection, by irritation, by internal stimulus or by some other cause;

The disease or disorder or the observable manifestation or manifestations of the disease or disorder are alleviated by alpha-2 activity. The lack of alpha-2 activity need not be causally related to the disease or disorder or the observable manifestations thereof;

Alpha-2 activity interferes with part of the biochemical or cellular cascade that results in or relates to the disease or disorder. In this respect, the alpha-2 activity alters the cascade, and thus controls the disease, condition or disorder.

The compounds of this invention are particularly useful for the treatment of nasal congestion associated with allergies, colds, and other nasal disorders, as well as the sequelae of congestion of the mucous membranes (for example, sinusitis and otitis media). At effective doses, it has been found that undesired side effects can be avoided.

While not limited to a particular mechanism of action, the subject compounds are believed to provide advantages in the treatment of nasal decongestion over related compounds through their ability to interact with alpha-2 adrenoceptors. The subject compounds have been found to be alpha-2 adrenoceptor agonists which cause constriction of peripheral vascular beds in the nasal turbinates.

Alpha-2 adrenoceptors are distributed both inside and outside of the central nervous system. Thus, though not essential for activity or efficacy, certain disorders preferably are treated with compounds that act on alpha-2 adrenoceptors in only one of these regions. Compounds of this invention vary in their ability to penetrate into the central nervous system and, thus, to produce effects mediated through central alpha-2 adrenoceptors. Thus, for example, a compound which displays a higher degree of central nervous system activity is preferred for central nervous system indications over other compounds as described below. However, even for compounds that exhibit primarily peripheral activity, central nervous system actions can be evoked by an increase in the dose of the compound. Further specificity of action of these compounds can be achieved by delivering the agent to the region where activity is desired (for example, topical administration to the eye, nasal mucosa or respiratory tract).

Compounds preferred for, but not limited to, the treatment of certain cardiovascular disorders, pain, substance abuse and/or withdrawal, ulcer and hyperacidity include those compounds that are centrally acting. By centrally acting what is meant is that they have some action on the alpha-2 adrenoceptors in the central nervous system in addition to their action at peripheral alpha-2 adrenoceptors.

Compounds preferred for, but not limited to, the treatment of respiratory disorders, ocular disorders, migraine, certain cardiovascular disorders, and certain other gastrointestinal disorders are peripherally acting. By peripherally acting, what is meant is that these compounds act primarily on alpha-2 adrenoceptors in the periphery, rather than those in the central nervous system. Methods are available in the art to determine which compounds are primarily peripherally acting and which are primarily centrally acting.

Thus, compounds of the subject invention are also useful for the treatment of ocular disorders such as ocular hypertension, glaucoma, hyperemia, conjunctivitis, and uveitis. The compounds are administered either perorally, or topically as drops, sprays, mists, gels or creams directly to the surface of the mammalian eye.

The compounds of this invention are also useful for controlling gastrointestinal disorders, such as diarrhea, irritable bowel syndrome, hyperchlorhydria and peptic ulcer.

The compounds of this invention are also useful for diseases and disorders associated with sympathetic nervous system activity, including hypertension, myocardial ischemia, cardiac reperfusion injury, angina, cardiac arrhythmia, heart failure and benign prostatic hypertrophy. Due to their sympatholytic effect, compounds are also useful as an adjunct to anesthesia during surgical procedures.

The compounds of this invention are also useful for relieving pain associated with various disorders. The compounds are administered perorally, parenterally, and/or by direct injection into the cerebrospinal fluid.

The compounds of this invention are also useful for the prophylactic or acute treatment of migraine. The compounds are administered perorally, parenterally or intranasally.

The compounds of this invention are also useful for treatment of substance abuse, in particular abuse of alcohol and opiates, and alleviating the abstinence syndromes evoked by withdrawal of these substances.

The compounds of this invention are also useful for other diseases and disorders where vasoconstriction, particularly of veins, would provide a benefit, including septic or cardiogenic shock, elevated intracranial pressure, hemmorhoids, venous insufficiency, varicose veins, and menopausal flushing.

The compounds of this invention are also useful for neurologic diseases and disorders, including spasticity, epilepsy, attention deficit hyperactive disorder, Tourette's syndrome, and cognitive disorders.

The pharmacological activity and selectivity of these compounds can be determined using published test procedures. The alpha-2 selectivity of the compounds is determined by measuring receptor binding affinities and in vitro functional potencies in a variety of tissues known to possess alpha-2 and/or alpha-1 receptors. (See, e.g., *The Alpha-2 Adrenergic Receptors*, L. E. Limbird, ed., Humana Press, Clifton, N.J.) The following in vivo assays are typically conducted in rodents or other species. Central nervous system activity is determined by measuring locomotor activity as an index of sedation. (See, e.g., Spyraki, C. & H. Fibiger, "Clonidine-induced Sedation in Rats: Evidence for Mediation by Postsynaptic Alpha-2 Adrenoreceptors", *Journal of Neural Transmission*, Vol. 54 (1982), pp. 153–163). Nasal decongestant activity is measured using rhinomanometry as an estimate of nasal airway resistance. (See, e.g., Salem, S. & E. Clemente, "A New Experimental Method for Evaluating Drugs in the Nasal Cavity", Archives of *Otolaryngology*, Vol. 96 (1972), pp. 524–529). Antiglaucoma activity is determined by measuring intraocular pressure. (See, e.g., Potter, D., "Adrenergic Pharmacology of Aqueous Human Dynamics", *Pharmacological Reviews*, Vol. 13 (1981), pp. 133–153). Antidiarrheal activity is determined by measuring the ability of the compounds to inhibit prostaglandin-induced diarrhea. (See, e.g., Thollander, M., P. Hellstrom & T. Svensson, "Suppression of Castor Oil-induced Diarrhea by Alpha-2 Adrenoceptor Agonists", *Alimentary Pharmacology and Therapeutics,* Vol. 5 (1991), pp. 255–262). Efficacy in treating irritable bowel syndrome is determined by measuring the ability of compounds to reduce the stress-induced increase in fecal output. (See, e.g., Barone, F., J. Deegan, W. Price, P. Fowler, J. Fondacaro & H. Ormsbee III, "Cold-restraint stress increases rat fecal pellet output and colonic transit", *American Journal of Physiology,* Vol. 258 (1990), pp. G329–G337). Antiulcer and reduction of hyperchlorhydria efficacy is determined by measuring the reduction in gastric acid secretion produced by these compounds (See, e.g., Tazi-Saad, K., J. Chariot, M. Del Tacca & C. Roze, "Effect of α2-adrenoceptor agonists on gastric pepsin and acid secretion in the rat", *British Journal of Pharmacology,* Vol. 106 (1992), pp. 790–796). Antiasthma activity is determined by measuring the effect of the compound on bronchoconstriction associated with pulmonary challenges such as inhaled antigens. (See, e.g., Chang, J. J. Musser & J. Hand, "Effects of a Novel Leukotriene $D_4$ Antagonist with 5-Lipoxygenase and Cyclooxygenase Inhibitory Activity, Wy-45,911, on Leukotriene-$D_4$- and Antigen-induced Bronchoconstriction in Guinea Pig", *International Archives of Allergy and Applied Immunology,* Vol. 86 (1988), pp. 48–54; and Delehunt, J., A. Perruchound, L. Yerger, B. Marchette, J. Stevenson & W. Abraham, "The Role of Slow-Reacting Substance of Anaphylaxis in the Late Bronchial Response After Antigen Challenge in Allergic Sheep", *American Reviews of Respiratory Disease,* Vol. 130 (1984), pp. 748–754). Activity in cough is determined by measuring the number and latency of the cough response to respiratory challenges such as inhaled citric acid. (See, e.g., Callaway, J. & R. King, "Effects of Inhaled α2-Adrenoceptor and $GABA_B$ Receptor Agonists on Citric Acid-Induced Cough and Tidal Volume Changes in Guinea Pigs", *European Journal of Pharmacology,* Vol. 220 (1992), pp. 187–195). The sympatholytic activity of these compounds is determined by measuring the reduction of plasma catecholamines (See, e.g., R. Urban, B. Szabo & K. Starke "Involvement of peripheral presynaptic inhibition in the reduction of sympathetic tone by moxonidine, rilmenidine and UK 14,304", *European Journal of Pharmacology,* Vol. 282 (1995), pp. 29–37) or the reduction in renal sympathetic nerve activity (See, e.g., Feng, Q., S. Carlsson, P. Thoren & T. Hedner, "Effects of clonidine on renal sympathetic nerve activity, natriuresis and diuresis in chronic congestive heart failure rats", *Journal of Pharmacology and Experimental Therapeutics,* Vol. 261 (1992), pp. 1129–1135), providing the basis for their benefit in heart failure and benign prostatic hypertrophy. The hypotensive effect of these compounds is measure directly as a reduction in mean blood pressure (See, e.g., Timmermans, P. & P. Van Zwieten, "Central and peripheral α-adrenergic effects of some imidazolidines", *European Journal of Pharmacology,* Vol. 45 (1977), pp. 229–236). Clinical studies have demonstrated the beneficial effect of alpha-2 agonists in the prevention of myocardial ischemia during surgery (See, e.g., Talke, P., J. Li, U. Jain, J. Leung, K. Drasner, M. Hollenberg & D. Mangano, "Effects of Perioperative Dexmedetomidine Infusion in Patients Undergoing Vascular Surgery", *Anesthesiology,* Vol. 82 (1995), pp. 620–633) and in the prevention of angina (See, e.g., Wright, R. A., P. Decroly, T. Kharkevitch & M. Oliver, "Exercise Tolerance in Angina is Improved by Mivazerol—an α2-Adrenoceptor Agonist", *Cardiovascular Drugs and Therapy,* Vol. 7 (1993), pp. 929–934). The efficacy of these compounds in cardiac reperfusion injury is demonstrated by measuring the reduction of cardiac necrosis and neutrophil infiltration (See, e.g., Weyrich, A., X. Ma, & A. Lefer, "The Role of L-Arginine in Ameliorating Reperfusion Injury After Myocardial Ischemia in the Cat", *Circulation,* Vol. 86 (1992), pp. 279–288). The cardiac antiarrhythmic effect of these compounds is demonstrated by measuring the inhibition of ouabain induced arrhythmias (See, e.g., Thomas, G. & P. Stephen, "Effects of Two Imidazolines (ST-91 and ST-93) on the Cardiac Arrhythmias and Lethality Induced by Ouabain in Guinea-Pig", *Asia-Pacific Journal of Pharmacology,* Vol. 8 (1993), pp.109–113; and Samson, R., J. Cai, E. Shibata, J. Martins & H. Lee, "Electrophysiological effects of α2-adrenergic stimulation in canine cardiac Purkinje fibers", *American Journal of Physiology,* Vol. 268 (1995), pp. H2024–H2035). The vasoconstrictor activity of these compounds is demonstrated by measuring the contractile properties on isolated arteries and veins in vitro (See, e.g., Flavahan, N., T. Rimele, J. Cooke & M. Vanhoutte, "Characterization of Postjunctional Alpha-1 and Alpha-2 Adrenoceptors Activated by Exogenous or Nerve-Released Norepinephrine in the Canine Saphenous Vein", *Journal of Pharmacology and Experimental Therapeutics,* Vol. 230 (1984), pp. 699–705). The effectiveness of these compounds at reducing intracranial pressure is demonstrated by measurement of this property in a canine model of subarachnoid hemorrhage (See, e.g., McCormick, J., P. McCormick, J. Zabramski & R. Spetzler, "Intracranial pressure reduction by a central alpha-2 adrenoreceptor agonist after subarachnoid hemorrhage", *Neurosurgery,* Vol. 32 (1993), pp. 974–979). The inhibition of menopausal flushing is demonstrated by measuring the reduction of facial blood flow in the rat (See, e.g., Escott, K., D. Beattie, H. Connor & S. Brain, "The modulation of the increase in rat facial skin blood flow observed after trigeminal ganglion stimulation", *European Journal of Pharmacology,* Vol. 284 (1995), pp. 69–76) as demonstrated for alpha-2 adrenergic agonists on cutaneous blood flow in the tail (See, e.g., Redfern, W., M. MacLean, R. Clague & J. McGrath, "The role of alpha-2 adrenoceptors in the vasculature of the rat tail", *British Journal of Pharmacology,* Vol. 114 (1995), pp. 1724–1730). The antinociceptive and pain reducing properties of these compounds is demonstrated by measuring the increase in pain threshold in the rodent writhing and hot plate antinociceptive models (See, e.g., Millan, M., K. Bervoets, J. Rivet, R. Widdowson, A. Renouard, S, Le Marouille-Girardon & A. Gobert, "Multiple Alpha-2 Adrenergic Receptor Subtypes. II. Evidence for a Role of Rat Alpha-2A Adrenergic Receptors in the Control of Nociception, Motor Behavior and Hippocampal Synthesis of Noradrenaline", *Journal of Pharmacology and Experimental Therapeutics,* Vol. 270 (1994), pp. 958–972). The antimigraine effect of these compounds is demonstrated by measuring the reduction of dural neurogenic inflammation to trigeminal ganglion stimulation in the rat (See, e.g., Matsubara, T., M. Moskowitz & Z. Huang, "UK-14,304, R(-)-alpha-methyl-histamine and SMS 201-995 block plasma protein leakage within dura mater by prejunctional mechanisms", *European Journal of Pharmacology,* Vol. 224 (1992), pp. 145–150). The ability of these compounds to suppress opiate withdrawal is demonstrated by measuring the suppression of enhanced sympathetic nerve activity (See, e.g., Franz, D., D. Hare & K. McCloskey, "Spinal sympathetic neurons: possible sites of opiate-withdrawal suppression by clonidine", *Science,* Vol. 215 (1982), pp. 1643–1645). Antiepileptic activity of these compounds is demonstrated by measuring the inhibition of the kindling response (See, e.g., Shouse, M., M. Bier, J. Langer, O. Alcalde, M. Richkind & R. Szymusiak, "The α2-agonist clonidine suppresses seizures, whereas the alpha-2 antagonist idazoxan promotes seizures—a microinfusion study in amygdala-kindled kittens", *Brain Research,* Vol. 648 (1994), pp. 352–356). The effectiveness of other alpha-2 agonists in the management of neurologic disorders has been demonstrated, including attention-deficit hyperactive disorder and Tourette's syndrome (See, e.g., Chappell P., M. Riddle, L. Scahill, K. Lynch, R. Schultz, A. Arnsten, J. Leckman & D. Cohen, "Guanfacine treatment of comorbid attention-deficit hyperactivity disorder and Tourette's syndrome: preliminary clinical experience", *Journal of American Academy of Child and Adolescent Psychiatry,* Vol. 34 (1995), pp. 1140–1146), cognitive disorders (See, e.g., Coull, J., "Pharmacological manipulations of the a2-noradrenergic system. Effects on cognition", *Drugs and Aging,* Vol. 5 (1994), pp. 116–126), and spasticity (See, e.g., Eyssette, M., F. Rohmer, G. Serratrice, J. Warter & D. Boisson, "Multicenter, double-blind trial of a novel antispastic agent, tizanidine, in spasticity associated with multiple sclerosis", *Current Medical Research & Opinion,* Vol. 10 (1988), pp. 699–708).

Another aspect of this invention involves methods for preventing or treating nasal congestion by administering a safe and effective amount of a subject compound to a mammal experiencing or at risk of experiencing nasal congestion. Such nasal congestion may be associated with human diseases or disorders which include, but are not limited to, seasonal allergic rhinitis, acute upper respiratory viral infections, sinusitis, perennial rhinitis, and vasomotor rhinitis. In addition, other disorders can be generally associated with mucous membrane congestion (for example, otitis media and sinusitis.) Each administration of a dose of the subject compound preferably administers a dose within the range of from about 0.0001 mg/kg to about 5 mg/kg of a compound, more preferably from about 0.001 mg/kg to about 0.5 mg/kg. Peroral administration of such doses is preferred. The frequency of administration of a subject compound according to this invention is preferably from about once to about six times daily, more preferably from about once to about 4 times daily. Such doses and frequencies are also preferred for treating other respiratory conditions, such as, cough, chronic obstructive pulmonary disease (COPD) and asthma. Such doses and frequencies are also preferred for treating conditions that are associated with mucous membrane congestion (for example, sinusitis and otitis media).

Another aspect of this invention involves methods for preventing or treating glaucoma by administering a safe and effective amount of a subject compound to a mammal experiencing or at risk of experiencing glaucoma. If administered systemically, each administration of a dose of the subject compound preferably administers a dose within the range of from about 0.0001 mg/kg to about 5 mg/kg of a compound, more preferably from about 0.001 mg/kg to about 0.5 mg/kg. If intraocular dosing is used then preferably one administers a typical volume (for example, 1 or 2 drops) of a liquid composition, comprising from about 0.0001% to about 5% of a subject compound, more preferably from about 0.01% to about 0.5% of the compound. Determination of the exact dosage and regimen is within the purview of the skilled artisan. Intraocular administration of such doses is preferred. The frequency of administration of a subject compound according to this invention is preferably from about once to about six times daily, more preferably from about once to about 4 times daily.

Another aspect of this invention involves methods for preventing or treating gastrointestinal disorders, such as diarrhea, irritable bowel syndrome, and peptic ulcer by administering a safe and effective amount of a subject compound to a mammal experiencing or at risk of experiencing gastrointestinal disorders. Each administration of a dose of the subject compound preferably administers a dose within the range of from about 0.0001 mg/kg to about 5 mg/kg of a compound, more preferably from about 0.001 mg/kg to about 0.5 mg/kg. Peroral administration of such doses is preferred. The frequency of administration of a subject compound according to this invention is preferably from about once to about six times daily, more preferably from about once to about 4 times daily.

Another aspect of this invention involves methods for preventing or treating migraine, by administering a safe and effective amount of a subject compound to a mammal experiencing or at risk of experiencing migraine. Each administration of a dose of the subject compound preferably administers a dose within the range of from about 0.0001 mg/kg to about 5 mg/kg of a compound, more preferably from about 0.001 mg/kg to about 0.5 mg/kg. Peroral, parenteral or intranasal administration of such doses is preferred. The frequency of peroral administration of a subject compound according to this invention is preferably from about once to about six times daily, more preferably from about once to about 4 times daily. The frequency of parenteral dosing of a subject compound according to this invention is preferably from about once to about six times daily, more preferably from about once to about 4 times daily or by infusion to the desired effect. The frequency of intranasal dosing of a subject compound according to this invention is preferably from about once to about six times daily, more preferably from about once to about 4 times daily.

Another aspect of this invention involves methods for preventing or treating disorders related to sympathetic nervous system activity, such as hypertension, myocardial ischemia, cardiac reperfusion injury, angina, cardiac arrhythmia, and benign prostatic hypertrophy, by administering a safe and effective amount of a subject compound to a mammal experiencing or at risk of experiencing these diseases or disorders. Each administration of a dose of the subject compound preferably administers a dose within the range of from about 0.0001 mg/kg to about 5 mg/kg of a compound, more preferably from about 0.001 mg/kg to about 0.5 mg/kg. Peroral and parenteral administration of such doses are preferred. The frequency of peroral administration of a subject compound according to this invention is preferably from about once to about six times daily, more preferably from about once to about 4 times daily. The frequency of parenteral dosing of a subject compound according to this invention is preferably from about once to about six times daily, more preferably from about once to about 4 times daily or by infusion to the desired effect.

Another aspect of this invention involves methods for preventing or treating pain, by administering a safe and effective amount of a subject compound to a mammal experiencing or at risk of experiencing pain. Each administration of a dose of the subject compound preferably administers a dose within the range of from about 0.0001 mg/kg to about 5 mg/kg of a compound, more preferably from about 0.001 mg/kg to about 0.5 mg/kg. Peroral or parenteral administration of such doses is preferred. The frequency of peroral administration of a subject compound according to this invention is preferably from about once to about six times daily, more preferably from about once to about 4 times daily. The frequency of parenteral dosing of a subject compound according to this invention is preferably from about once to about six times daily, more preferably from about once to about 4 times daily or by infusion to the desired effect.

Another aspect of this invention involves methods for preventing or treating substance abuse and the abstinence syndrome resulting from withdrawal of these substances, such as alcohol and opiates, by administering a safe and effective amount of a subject compound to a mammal experiencing or at risk of experiencing substance abuse or withdrawal symptoms. Each administration of a dose of the subject compound preferably administers a dose within the range of from about 0.0001 mg/kg to about 5 mg/kg of a compound, more preferably from about 0.001 mg/kg to about 0.5 mg/kg. Peroral administration of such doses is preferred. The frequency of administration of a subject compound according to this invention is preferably from about once to about six times daily, more preferably from about once to about 4 times daily.

Composition and Method Examples

The following non-limiting examples illustrate the compositions and methods of use of this invention.

Example A

Oral Tablet Composition

| Ingredient | Amount per tablet (mg) |
|---|---|
| Subject Compound 4 | 20.0 |
| Microcrystalline cellulose (Avicel PH 102 ®) | 80.0 |
| Dicalcium phosphate | 96.0 |
| Pyrogenic silica (Cab-O-Sil ®) | 1.0 |
| Magnesium stearate | 3.0 |
| Total = | 200.0 mg |

One tablet is swallowed by a patient with nasal congestion. The congestion is substantially diminished.

Other compounds having a structure according to Formula I are used with substantially similar results.

Example B

Chewable Tablet Composition

| Ingredient | Amount per tablet (mg) |
|---|---|
| Subject Compound 1 | 15.0 |
| Mannitol | 255.6 |
| Microcrystalline cellulose (Avicel PH 101 ®) | 100.8 |
| Dextrinized sucrose (Di-Pac ®) | 199.5 |
| Imitation orange flavor | 4.2 |
| Sodium saccharin | 1.2 |
| Stearic acid | 15.0 |
| Magnesium stearate | 3.0 |
| FD&C Yellow #6 dye | 3.0 |
| Pyrogenic silica (Cab-O-Sil ®) | 2.7 |
| Total = | 600.0 mg |

One tablet is chewed and swallowed by a patient with nasal congestion. The congestion is substantially reduced.

Other compounds having a structure according to Formula I are used with substantially similar results.

Example C

Sublingual Tablet Composition

| Ingredient | Amount per tablet (mg) |
|---|---|
| Subject Compound 5 | 2.00 |
| Mannitol | 2.00 |
| Microcrystalline cellulose (Avicel PH 101 ®) | 29.00 |
| Mint flavorants | 0.25 |
| Sodium saccharin | 0.08 |
| Total = | 33.33 mg |

One tablet is placed under the tongue of a patient with nasal congestion and allowed to dissolve. The congestion is rapidly and substantially diminished.

Other compounds having a structure according to Formula I are used with substantially similar results.

Example D

Intranasal Solution Composition

| Ingredient | Composition (% w/v) |
|---|---|
| Subject Compound 3 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

One-tenth of a mL of the composition is sprayed from a pump actuator into each nostril of a patient with nasal congestion. The congestion is substantially diminished.

Other compounds having a structure according to Formula I are used with substantially similar results.

Example E

Intranasal Gel Composition

| Ingredient | Composition (% w/v) |
|---|---|
| Subject Compound 1 | 0.10 |
| Benzalkonium chloride | 0.02 |
| Thimerosal | 0.002 |
| Hydroxypropyl methylcellulose (Metolose 65SH4000 ®) | 1.00 |
| Aromatics | 0.06 |
| Sodium chloride (0.65%) | q.s. |
| Total = | 100.00 |

One-fifth of a mL of the composition is applied as drops from a dropper into each nostril of a patient with riasal congestion. The congestion is substantially reduced.

Other compounds having a structure according to Formula I are used with substantially similar results.

Example F

Inhalation Aerosol Composition

| Ingredient | Composition (% w/v) |
| --- | --- |
| Subject Compound 2 | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

Two-puffs of the aerosol composition is inhaled from a metered-dose inhaler by a patient with asthma. The asthmatic condition is effectively relieved.

Other compounds having a structure according to Formula I are used with substantially similar results.

Example G

Topical Ophthalmic Composition

| Ingredient | Composition (% w/v) |
| --- | --- |
| Subject Compound 5 | 0.10 |
| Benzalkonium chloride | 0.01 |
| EDTA | 0.05 |
| Hydroxyethylcellulose (Natrosol M ®) | 0.50 |
| Sodium metabisulfite | 0.10 |
| Sodium chloride (0.9%) | q.s. |
| Total = | 100.0 |

One-tenth of a mL of the composition is administered directly into each eye of a patient with glaucoma. The intraocular pressure is substantially reduced.

Other compounds having a structure according to Formula I are used with substantially similar results.

Example H

Oral Liquid Composition

| Ingredient | Amount/15 mL Dose |
| --- | --- |
| Subject Compound 4 | 15 mg |
| Chlorpheniramine maleate | 4 mg |
| Propylene glycol | 1.8 g |
| Ethanol (95%) | 1.5 mL |
| Methanol | 12.5 mg |
| Eucalyptus oil | 7.55 mg |
| Flavorants | 0.05 mL |
| Sucrose | 7.65 g |
| Carboxymethylcellulose (CMC) | 7.5 mg |
| Microcrystalline cellulose and Sodium CMC (Avicel RC 591 ®) | 187.5 mg |
| Polysorbate 80 | 3.0 mg |
| Glycerin | 300 mg |
| Sorbitol | 300 mg |
| FD&C Red #40 dye | 3 mg |
| Sodium saccharin | 22.5 mg |
| Sodium phosphate monobasic | 44 mg |
| Sodium citrate monohydrate | 28 mg |
| Purified Water | p.s. |
| Total = | 15 mL |

One 15 mL dose of the liquid composition is swallowed by a patient with nasal congestion and runny nose due to allergic rhinitis. The congestion and runny nose are effectively reduced.

Other compounds having a structure according to Formula I are used with substantially similar results.

Example J

Oral Liquid Composition

| Ingredient | Amount/15 mL Dose |
| --- | --- |
| Subject Compound 2 | 30 mg |
| Sucrose | 8.16 g |
| Glycerin | 300 mg |
| Sorbitol | 300 mg |
| Methylparaben | 19.5 mg |
| Propylparaben | 4.5 mg |
| Menthol | 22.5 mg |
| Eucalyptus oil | 7.5 mg |
| Flavorants | 0.07 mL |
| FD&C Red #40 dye | 3.0 mg |
| Sodium saccharin | 30 mg |
| Purified water | q.s. |
| Total = | 15 mL |

One 15 mL dose of the alcohol-free liquid medication is swallowed by a patient with nasal congestion. The congestion is substantially diminished.

Other compounds having a structure according to Formula I are used with substantially similar results.

Example K

Oral Tablet Composition

| Ingredient | Amount per tablet (mg) |
| --- | --- |
| Subject Compound 1 | 4 |
| Microcrystalline cellulose, NF | 130 |
| Starch 1500, NF | 100 |
| Magnesium stearate, USP | 2 |
| Total = | 236 mg |

One tablet is swallowed by a patient with migraine. The pain and aura of migraine is substantially diminished.

Other compounds having a structure according to Formula I are used with substantially similar results.

Example L

Oral Tablet Composition

| Ingredient | Amount per tablet (mg) |
| --- | --- |
| Subject Compound 2 | 12 |
| Hydroxypropyl methylcellulose, USP | 12 |
| Magnesium stearate, USP | 2 |
| Lactose anhydrous, USP | 200 |
| Total = | 226 mg |

For the relief of pain. Adults 12 and over take one tablet every twelve hours.

Other compounds having a structure according to Formula I are used with substantially similar results.

Example M

Oral Caplet Composition

| Ingredient | Amount per tablet (mg) |
| --- | --- |
| Naproxen sodium anhydrous, USP | 220 |
| Subject Compound 3 | 6 |
| Hydroxypropyl methylcellulose, USP | 6 |
| Magnesium stearate, USP | 2 |
| Povidone K-30, USP | 10 |
| Talc, USP | 12 |
| Microcrystalline cellulose, NF | 44 |
| Total = | 300 mg |

For relief of symptoms associated with the common cold, sinusitis, or flu including nasal congestion, headache, fever, body aches, and pains. Adults 12 and over take two caplets every twelve hours.

Other compounds having a structure according to Formula I are used with substantially similar results.

Example N

Oral Tablet Composition

| Ingredient | Amount per tablet (mg) |
| --- | --- |
| Subject Compound 4 | 6 |
| Hydroxypropyl methylcellulose, USP | 6 |
| Silicon dioxide, colloidal, NF | 30 |
| Pregelatinized starch, NF | 50 |
| Magnesium stearate, USP | 4 |
| Total = | 96 mg |

For treatment of benign prostatic hypertrophy. Take one tablet per day.

Other compounds having a structure according to Formula I are used with substantially similar results.

Example O

Oral Tablet Composition

| Ingredient | Amount per caplet (mg) |
| --- | --- |
| Subject Compound 5 | 6 |
| Hydroxypropyl methylcellulose, USP | 6 |
| Magnesium stearate, USP | 2 |
| Povidone K-30, USP | 10 |
| Talc, USP | 12 |
| Microcrystalline cellulose, NF | 44 |
| Total = | 80 mg |

For the use in the treatment of alcoholism or opiate addiction. Adults 12 and over take two caplets every twelve hours.

Other compounds having a structure according to Formula I are used with substantially similar results.

Example P

Oral Tablet Composition

| Ingredient | Amount per tablet (mg) |
| --- | --- |
| Subject Compound 1 | 6 |
| Hydroxypropyl methylcellulose, USP | 12 |
| Magnesium stearate, USP | 2 |
| Povidone K-30, USP | 10 |
| Talc, USP | 12 |
| Microcrystalline cellulose, NF | 44 |
| Total = | 86 mg |

For the treatment of ulcer and hyperacidity. Take two tablets as appropriate.

Other compounds having a structure according to Formula I are used with substantially similar results.

Example Q

Oral Tablet Composition

| Ingredient Component | Amount per tablet (mg) Amount |
| --- | --- |
| Subject Compound 5 | 10 mg/ml carrier |
| Carrier: | |
| Sodium citrate buffer with (percent by weight of carrier): | |
| Lecithin | 0.48% |
| Carboxymethylcellulose | 0.53 |
| Povidone | 0.50 |
| Methyl paraben | 0.11 |
| Propyl paraben | 0.011 |

For the reduction of cardiac reperfusion injury.

Other compounds having a structure according to Formula I are used with substantially similar results.

Example R

Oral Liquid Composition

| Ingredient | Amount/fl oz Dose (mg) |
| --- | --- |
| Acetaminophen, USP | 1000 |
| Doxylamine succinate, USP | 12.5 |
| Dextromethorphan hydrobromide, USP | 30 |
| Subject Compound 2 | 6 |
| Dow XYS-40010.00 resin | 3 |
| High fructose corn syrup | 16000 |
| Polyethylene glycol, NF | 3000 |
| Propylene glycol, USP | 3000 |
| Alcohol, USP | 2500 |
| Sodium citrate dihydrate, USP | 150 |
| Citric acid, anhydrous, USP | 50 |
| Saccharin sodium, USP | 20 |
| Flavor | 3.5 |
| Purified water, USP | 3500 |
| Total = | 29275 mg/fl oz |

For the relief of minor aches, pains, headache, muscular aches, sore throat pain, and fever associated with a cold or flu. Relieves nasal congestion, cough due to minor throat and bronchial irritations, runny nose, and sneezing associated with the common cold. Adults 12 and over take one fluid ounce every six hours.

Example S

Oral Liquid Composition

| Ingredient | Amount/fl oz Dose (mg) |
|---|---|
| Naproxen sodium anhydrous, USP | 220 |
| Doxylamine succinate, USP | 12.5 |
| Dextromethorphan hydrobromide, uSP | 30 |
| Subject Compound 1 | 6 |
| Dow XYS-40010.00 resin | 3 |
| High fructose corn syrup | 16000 |
| Polyethylene glycol, NF | 3000 |
| Propylene glycol, USP | 3000 |
| Alcohol, USP | 2500 |
| Sodium citrate dihydrate, USP | 150 |
| Citric acid, anhydrous, USP | 50 |
| Saccharin sodium, USP | 20 |
| Flavor | 3.5 |
| Purified water, USP | 3800 |
| Total = | 28795 mg/fl oz |

For the relief of minor aches, pains, headache, muscular aches, sore throat pain, and fever associated with a cold or flu. Relieves nasal congestion, cough due to minor throat and bronchial irritations, runny nose, and sneezing associated with the common cold. Adults 12 and over take one fluid ounce every six hours.

Other compounds having a structure according to Formula I are used with substantially similar results.

COMPOSITION EXAMPLE T

A composition for parenteral administration, according to this invention, is made comprising:

| Component | Amount |
|---|---|
| Subject Compound 1 | 10 mg/ml carrier |
| Carrier: | |
| Sodium citrate buffer with (percent by weight of carrier): | |
| Lecithin | 0.48% |
| Carboxymethylcellulose | 0.53 |
| Povidone | 0.50 |
| Methyl paraben | 0.11 |
| Propyl paraben | 0.011 |

The above ingredients are mixed, forming a solution. Approximately 2.0 ml of the solution is administered, intravenously, to a human subject suffering from septic or cardiogenic shock. The symptoms subside.

Other compounds having a structure according to Formula I are used with substantially similar results.

Example U

Oral Tablet Composition

| Ingredient | Amount per tablet (mg) |
|---|---|
| Subject Compound 5 | 10 |
| Hydroxypropyl methylcellulose, USP | 12 |
| Magnesium stearate, USP | 2 |
| Povidone K-30, USP | 10 |
| Talc, USP | 12 |
| Microcrystalline cellulose, NF | 44 |
| Total = | 90 mg |

For the treatment of cardiac arrhythmia. Take as prescribed.

Other compounds having a structure according to Formula I are used with substantially similar results.

Example V

Oral Tablet Composition

| Ingredient | Amount per tablet (mg) |
|---|---|
| Subject Compound 1 | 4 |
| Microcrystalline cellulose, NF | 130 |
| Starch 1500, NF | 100 |
| Magnesium stearate, USP | 2 |
| Total = | 236 mg |

For the treatment of congestive heart failure. Take as prescribed.

Other compounds having a structure according to Formula I are used with substantially similar results.

Modification of the preceding embodiments is within the scope of the skilled artisan in formulation, given the guidance of the specification in light of the state of the art.

Other examples of combination actives are contemplated. Examples of medicaments which can be combined with the primary active are included in U.S. Pat. No. 4,552,899 to Sunshine, et al., hereby incorporated by reference. All other references referred to throughout this specification are hereby incorporated by reference.

While particular embodiments of this invention have been described, it will be obvious to those skilled in the art that various changes and modifications of this invention can be made without departing from the spirit and scope of the invention. It is intended to cover, in the appended claims, all such modifications that are within the scope of this invention.

What is claimed is:

1. A compound of formula:

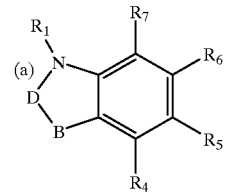

wherein:
 a) R1 is hydrogen; or alkyl or nil; where R1 is nil, bond (a) is a double bond;
 b) D is CR2 and R2 is selected from hydrogen; unsubstituted C1–C3 alkanyl; amino, hydroxy, mercapto; C1–C3 alkylthio or alkoxy; C1–C3 alkylamino or C1–C3 dialkylamino and halo;

c) B is CR3=CR8 or CR3=N wherein R3 and R8 are each independently selected from hydrogen; unsubstituted C1–C3 alkanyl, alkenyl or alkynyl; cycloalkanyl, cycloalkenyl; unsubstituted C1–C3 alkylthio or alkoxy; hydroxy; thio; nitro; cyano; amino; C1–C3 alkylamino or C1–C3 dialkylamino and halo;

d) R4, R5, and R6 are each independently selected from hydrogen; unsubstituted C1–C3 alkanyl, alkenyl or alkynyl; cycloalkanyl, cyclalkenyl; unsubstituted C1–C3 alkylthio or alkoxy; hydroxy; thio; nitro; cyano; amino; C1–C3 alkylamino or C1–C3 dialkylamino; halo; and NH—C(=NR10)NHR11 (guanidinyl); wherein R10 and R11 are independently selected from hydrogen; methyl; and ethyl; and wherein one and only one of R4, R8, and R6 is guanidinyl;

e) R1 is hydrogen or alkyl when B is CR3=CR8 and R4 or R5 is guanidinyl, and B is CR3=N and R6 is guanidinyl;

f) R7 is selected from hydrogen; unsubstituted C1–C3 alkanyl, alkenyl or alkynyl; cycloalkanyl, cycloalkenyl; unsubstituted C1–C3 alkythio or alkoxy; hydroxy; thio; nitro; cyano; amino; C1–C3 alkylamino or C1–C3 dialkylamino and halo;

or its enantiomer, optical isomer, stereoisomer, diastereomer, tautomer, addition salt, or biohydrolyzable amide or ester.

2. A compound according to claim 1, wherein $R_6$ is guanidinyl and $R_{11}$ is hydrogen.

3. A compound according to claim 2, wherein:
$R_2$ and $R_{10}$ are each independently chosen from hydrogen and methyl;
$R_4$ is selected from hydrogen, methyl, methoxy, fluoro, chloro, bromo and cyano;
$R_5$ is selected from hydrogen, methyl, chloro and bromo;
$R_7$ is selected from methyl, chloro, and bromo.

4. A compound according to claim 3, wherein R5 is hydrogen.

5. A compound according to claim 4, wherein B is CR3=CR8.

6. A compound according to claim 4, wherein
B is CR3=N; and
(a) is a double bond.

7. The compound according to claim 1, wherein $R_5$ is guanidinyl and $R_{11}$ is hydrogen.

8. A compound according to claim 7, wherein
$R_2$ and $R_{10}$ are each independently chosen from hydrogen and methyl;
$R_4$ is selected from methyl, chloro, and bromo;
$R_6$ is hydrogen; and
$R_7$ is selected from methyl, methoxy, chloro, bromo, and cyano.

9. A compound according to claim 8, wherein B is CR3=CR8.

10. A compound according to claim 8, wherein B is CR3=N.

11. The compound according to claim 1, wherein $R_4$ is guanidinyl.

12. The compound according to claim 11, wherein:
$R_5$, $R_6$ and $R_7$ are each independently selected from hydrogen; methyl; ethyl; methoxy; methylthio; thio; cyano; amino, and halo; and
$R_2$ is hydrogen.

13. A compound according to claim 12, wherein B is CR3=CR8.

14. A compound according to claim 12, wherein B is CR3=N.

15. The compound according to claim 1, wherein the compound is: (8-Methylquinolin-7-yl)guanidine; or (8-Bromoquinolin-7-yl)guanidine.

16. A pharmaceutical composition comprising:
(a) a safe and effective amount of a compound of a compound of formula:

wherein:
a. R1 is hydrogen; or alkyl or nil; where R1 is nil, bond (a) is a double bond;
b. D is CR2 and R2 is selected from hydrogen; unsubstituted C1–C3 alkanyl; amino, hydroxy, mercapto; C1–C3 alkylthio or alkoxy; C1–C3 alkylamino or C1–C3 dialkylamino and halo;
c. B is CR3=CR8 or CR3=N wherein R3 and R8 are each independently selected from hydrogen; unsubstituted C1–C3 alkanyl, alkenyl or alkynyl; cycloalkanyl, cycloalkenyl; unsubstituted C1–C3 alkylthio or alkoxy; hydroxy; thio; nitro; cyano; amino; C1–C3 alkylamino or C1–C3 dialkylamino and halo;
d. R4, R5, and R6 are each independently selected from hydrogen; unsubstituted C1–C3 alkanyl, alkenyl or alkynyl; cycloalkanyl, cyclalkenyl; unsubstituted C1–C3 alkylthio or alkoxy; hydroxy; thio; nitro; cyano; amino; C1–C3 alkylamino or C1–C3 dialkylamino; halo; and NH—C(=NR10)NHR11 (guanidinyl); wherein R10 and R11 are independently selected from hydrogen; methyl; and ethyl; and wherein one and only one of R4, R5, and R6 is guanidinyl;
e. R1 is hydrogen or alkyl when B is CR3=N and R6 is guanidinyl;
f. R7 is selected from hydrogen; unsubstituted C1–C3 alkanyl, alkenyl or alkynyl; cycloalkanyl, cycloalkenyl; unsubstituted C1–C3 alkythio or alkoxy; hydroxy; thio; nitro; cyano; amino; C1–C3 alkylamino or C1–C3 dialkylamino and halo;

or its enantiomer, optical isomer, stereoisomer, diastereomer, tautomer, addition salt, or biohydrolyzable amide or ester; and
(b) a pharmaceutically-acceptable carrier.

17. A pharmaceutical composition according to claim 16 further comprising one or more actives chosen from the group consisting of an antihistamine, antitussive, mast cell stabilizer, leukotriene antagonist, expectorant/mucolytic, antioxidant or radical inhibitor, steroid, bronchodilator, antiviral, analgesic, antiinflammatory, gastrointestinal and ocular active.

18. A pharmaceutical composition according to claim 16 further comprising an antihistamine.

19. A pharmaceutical composition according to claim 16 further comprising an antiinflammatory.

20. A method for preventing or treating a disorder modulated by alpha-2 adrenoceptors, by administering to a mammal in need of such treatment, a safe and effective amount of an alpha-2 adrenoceptor agonist compound according to formula:

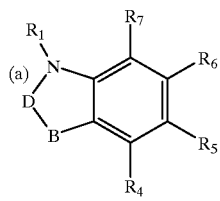

wherein:
  a) R1 is hydrogen; or alkyl or nil; where R1 is nil, bond (a) is a double bond;
  b) D is CR2 and R2 is selected from hydrogen; unsubstituted C1–C3 alkanyl; amino, hydroxy, mercapto; C1–C3 alkylthio or alkoxy; C1–C3 alkylamino or C1–C3 dialkylamino and halo;
  c) B is CR3=CR8 or CR3=N wherein R3 and R8 are each independently selected from hydrogen; unsubstituted C1–C3 alkanyl, alkenyl or alkynyl; cycloalkanyl, cycloalkenyl; unsubstituted C1–C3 alkylthio or alkoxy; hydroxy; thio; nitro; cyano; amino; C1–C3 alkylamino or C1–C3 dialkylamino and halo;
  d) R4, R5, and R6 are each independently selected from hydrogen; unsubstituted C1–C3 alkanyl, alkenyl or alkynyl; cycloalkanyl, cyclalkenyl; unsubstituted C1–C3 alkylthio or alkoxy; hydroxy; thio; nitro ; cyano; amino; C1–C3 alkylamino or C1–C3 dialkylamino; halo; and NH—C(=NR10)NHR11 (guanidinyl); wherein R10 and R11 are independently selected from hydrogen; methyl; and ethyl; and wherein one and only one of R4, R5, and R6 is guanidinyl;
  e) R1 is hydrogen or alkyl when B is CR3=N and R6 is guanidinyl;
  f) R7 is selected from hydrogen; unsubstituted C1–C3 alkanyl, alkenyl or alkynyl; cycloalkanyl, cycloalkenyl; unsubstituted C1–C3 alkythio or alkoxy; hydroxy; thio; nitro; cyano; amino; C1–C3 alkylamino or C1–C3 dialkylamino and halo;
or its enantiomer, optical isomer, stereoisomer, diastereomer, tautomer, addition salt, or biohydrolyzable amide or ester.

21. A method according to claim 20 wherein the disorder modulated by alpha-2 adrenoceptors is chosen from the groups comprising nasal congestion, otitis media, sinusitis, asthma, pain, migraine, substance abuse and addiction, gastrointestinal disorder, ulcer, stomach hyperacidity, benign prostatic hypertrophy.

22. The method of claim 21, wherein the disorder is nasal congestion.

23. The method of claim 21, wherein the disorder is otitis media.

24. The method of claim 21, wherein the disorder is sinusitis.

25. The method of claim 21, wherein the disorder is migraine.

26. The method of claim 21, wherein the disorder is pain.

27. The method of claim 20, wherein the disorder modulated by alpha-2 adrenoceptors is an ocular disorder.

28. The method of claim 27, wherein the ocular disorder is chosen from the group comprising ocular hypertension, glaucoma, hyperemia, conjunctivitis, and uveitis and glaucoma.

29. The method of claim 28, wherein the ocular disorder is glaucoma.

30. The method of claim 20, wherein the disorder modulated by alpha-2 adrenoceptors is a gastrointestinal disorder.

31. The method of claim 30, wherein the gastrointestinal disorder is chosen from the group comprising diarrhea and irritable bowel syndrome.

32. The method of claim 31, wherein the gastrointestinal disorder is diarrhea.

33. A method of treating or preventing a respiratory disorder, wherein the respiratory disorder is chosen from the group comprising cough, chronic obstructive pulmonary disease and asthma, by administering to a mammal in need of such treatment, a safe and effective amount of a compound according to formula:

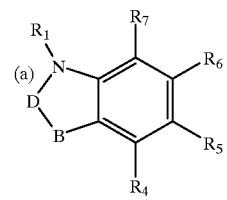

wherein
  a) R1 is hydrogen; or alkyl or nil; where R1 is nil, bond (α) is a double bond;
  b) D is CR2 and R2 is selected from hydrogen; unsubstituted C1–C3 alkanyl; amino, hydroxy, mercapto; C1–C3 alkylthio or alkoxy; C1–C3 alkylamino or C1–C3 dialkylamino and halo;
  c) B is CR3=CR8 or CR3=N wherein R3 and R8 are each independently selected from hydrogen; unsubstituted C1–C3 alkanyl, alkeny, or alkynyl; cycloalkanyl, cycloalkenyl; unsubstituted C1–C3 alkylthio or alkoxy; hydroxy; thio; nitro; cyano; amino; C1–C3 alkylamino or C1–C3 dialkylamino and halo;
  d) R4, R5, and R6 are each independently selected from hydrogen; unsubstituted C1–C3 alkanyl, alkenyl or alkynyl; cycloalkanyl, cyclalkenyl; unsubstituted C1–C3 alkylthio or alkoxy; hydroxy; thio; nitro; cyano; amino; C1–C3 alkylamino or C1–C3 dialkylamino; halo; and NH—C(=NR10)NHR11 (guanidinyl); wherein R10 and R11 are independently selected from hydrogen; methyl; and ethyl; and wherein one and only one of R4, R5, and R6 is guanidinyl;
  e) R1 is hydrogen or alkyl when B is CR3=N and R6 is guanidinyl;
  f) R7 is selected from hydrogen; unsubstituted C1–C3 alkanyl, alkenyl or alkynyl; cycloalkanyl, cycloalkenyl; unsubstituted C1–C3 alkythio or alkoxy; hydroxy; thio; nitro; cyano; amino; C1–C3 alkylamino or C1–C3 dialkylamino and halo;
or its enantiomer, optical isomer, stereoisomer, diastereomer, tautomer, addition salt, or biohydrolyzable amide or ester.

34. The method of claim 33, wherein the respiratory disorder is asthma.

35. A method for preventing or treating disorders mediated by sympathetic activity and modulated by alpha-2 adrenoceptors by administering to a mammal in need of such treatment, a safe and effective amount of an alpha-2 adrenoceptor agonist compound according to formula:

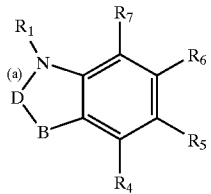

wherein:
- a) R1 is hydrogen; or alkyl or nil; where R1 is nil, bond (a) is a double bond;
- b) D is CR2 and R2 is selected from hydrogen; unsubstituted C1–C3 alkanyl; amino, hydroxy, mercapto; C1–C3 alkylthio or alkoxy; C1–C3 alkylamino or C1–C3 dialkylamino and halo;
- c) B is CR3=CR8 or CR3=N wherein R3 and R8 are each independently selected from hydrogen; unsubstituted C1–C3 alkanyl, alkenyl or alkynyl; cycloalkanyl, cycloalkenyl; unsubstituted C1–C3 alkylthio or alkoxy; hydroxy; thio; nitro; cyano; amino; C1–C3 alkylamino or C1–C3 dialkylamino and halo;
- d) R4, R5, and R6 are each independently selected from hydrogen; unsubstituted C1–C3 alkanyl, alkenyl or alkynyl; cycloalkanyl, cyclalkenyl; unsubstituted C1–C3 alkylthio or alkoxy; hydroxy; thio; nitro; cyano; amino; C1–C3 alkylamino or C1–C3 dialkylamino; halo; and NH—C(=NR10)NHR11 (guanidinyl); wherein R10 and R11 are independently selected from hydrogen; methyl; and ethyl; and wherein one and only one of R4, R5, and R6 is guanidinyl;
- e) R1 is hydrogen or alkyl B is CR3=N and R6 is guanidinyl;
- f) R7 is selected from hydrogen; unsubstituted C1–C3 alkanyl, alkenyl or alkynyl; cycloalkanyl, cycloalkenyl; unsubstituted C1–C3 alkythio or alkoxy; hydroxy; thio; nitro; cyano; amino; C1–C3 alkylamino or C1–C3 dialkylamino and halo;

or its enantiomer, optical isomer, stereoisomer, diastereomer, tautomer, addition salt, or biohydrolyzable amide or ester.

36. The method of claim 35, wherein the disorder mediated by sympathetic activity and modulated by alpha-2 adrenoceptors is chosen from the group comprising benign prostatic hypertrophy, myocardial ischemia, cardiac reperfusion injury, angina, cardiac arrhythmia, heart failure and hypertension.

37. The method of claim 36, wherein the disorder is heart failure.

38. A method for preventing or treating pain by administering to a mammal in need of such treatment, a safe and effective amount of a compound according to claim 1.

39. A method for preventing or treating migraine by administering to a mammal in need of such treatment, a safe and effective amount of a compound according to claim 1.

40. A method for treating substance abuse by administering to a mammal in need of such treatment, a safe and effective amount of a compound according to claim 1.

* * * * *

UNITED STATES PATENT AND TRADEMARK OFFICE
CERTIFICATE OF CORRECTION

PATENT NO. : 6,391,878 B2
DATED : May 21, 2002
INVENTOR(S) : Thomas Lee Cupps et al.

It is certified that error appears in the above-identified patent and that said Letters Patent is hereby corrected as shown below:

Column 2,
Line 67, delete "$R_g$" and insert -- $R_9$ --.

Column 13,
Line 60, delete "19" and insert -- 1g --.

Column 18,
Line 22, delete "Bromoguinolin" and insert -- Bromoquinolin --.

Column 20,
Line 29, delete "amino4" and insert -- amino-4 --.

Signed and Sealed this

Twenty-fourth Day of February, 2004

JON W. DUDAS
*Acting Director of the United States Patent and Trademark Office*